(12) United States Patent
Wozney et al.

(10) Patent No.: US 9,856,305 B2
(45) Date of Patent: Jan. 2, 2018

(54) DESIGNER OSTEOGENIC PROTEINS

(71) Applicant: WYETH LLC, New York, NY (US)

(72) Inventors: John Wozney, Hudson, MA (US); Howard Seeherman, Cambridge, MA (US); Christopher Todd Brown, Chelmsford, MA (US)

(73) Assignee: WYETH LLC, New York, NY (US)

( * ) Notice: Subject to any disclaimer, the term of this patent is extended or adjusted under 35 U.S.C. 154(b) by 0 days.

(21) Appl. No.: 14/679,705

(22) Filed: Apr. 6, 2015

(65) Prior Publication Data
US 2016/0052984 A1 Feb. 25, 2016

Related U.S. Application Data

(63) Continuation-in-part of application No. 14/589,468, filed on Jan. 5, 2015, now Pat. No. 9,688,735, which is a continuation of application No. 13/211,755, filed on Aug. 17, 2011, now Pat. No. 8,952,131.

(60) Provisional application No. 61/375,636, filed on Aug. 20, 2010.

(51) Int. Cl.
*A61K 38/18* (2006.01)
*C07K 14/51* (2006.01)
*C12N 15/09* (2006.01)
*A61K 38/00* (2006.01)

(52) U.S. Cl.
CPC .......... *C07K 14/51* (2013.01); *A61K 38/1875* (2013.01); *C12N 15/09* (2013.01); *A61K 38/00* (2013.01)

(58) Field of Classification Search
None
See application file for complete search history.

(56) References Cited

PUBLICATIONS

Kirsch et al., EMBO J., 2000, 19(13):3314-3324.*

* cited by examiner

*Primary Examiner* — Xiaozhen Xie

(57) ABSTRACT

The invention relates to novel designer osteogenic proteins having altered affinity for a cognate receptor, nucleic acids encoding the same, and methods of use therefor. More preferably, the novel designer osteogenic proteins are designer BMPs and have altered affinity for a cognate BMP receptor. The designer BMPs demonstrate altered biological characteristics and provide potential useful novel therapeutics.

10 Claims, 5 Drawing Sheets

Figure 1

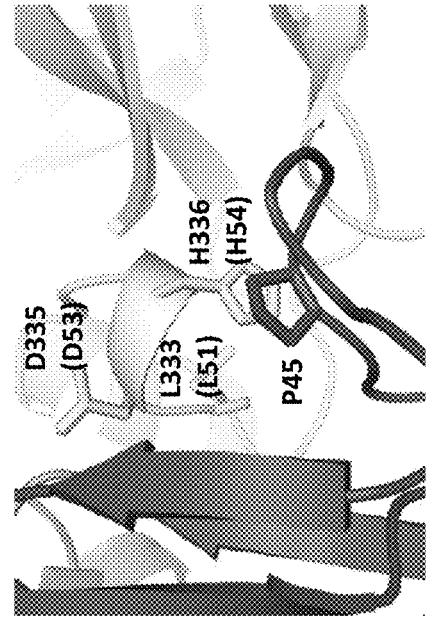
FIG. 3A CHO BMP2
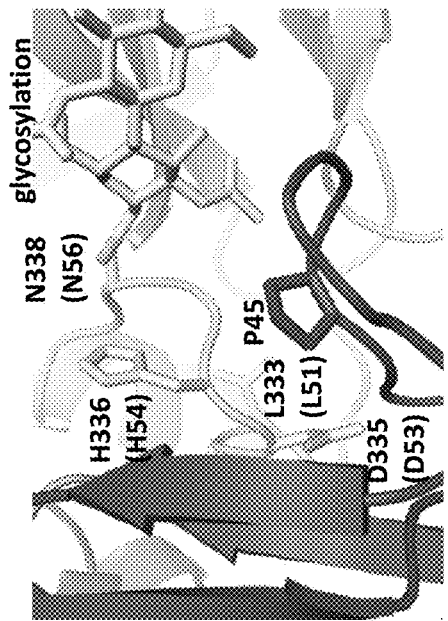
FIG. 3B E coli BMP2

DESIGNER OSTEOGENIC PROTEINS

CROSS-REFERENCE TO RELATED APPLICATIONS

This application is a continuation-in-part of, and claims the benefit of priority under 35 U.S.C. §120 to, U.S. patent application Ser. No. 14/589,468 filed Jan. 5, 2015 by Berasi et al., which is a continuation of U.S. patent application Ser. No. 13/211,755 filed Aug. 17, 2011 now U.S. Pat. No. 8,952,131, which in turn claims the benefit of priority under 35 U.S.C §119(e) to U.S. Provisional Patent Application No. 61/375,636, filed Aug. 20, 2010. Each of the foregoing applications are incorporated by reference herein in their entirety and for all purposes.

SEQUENCE LISTING

The instant application contains a Sequence Listing which has been submitted electronically in ASCII format and is hereby incorporated by reference in its entirety. Said ASCII copy, created on Apr. 3, 2015, is named 7362174001 and is 17,395 bytes in size.

FIELD OF THE INVENTION

This application relates to the field of osteogenic proteins, methods of making improved osteogenic proteins, and methods of treating patients with osteogenic proteins.

BACKGROUND OF THE INVENTION

The cystine knot cytokine superfamily is divided into subfamilies, which include, the transforming growth factor δ (TGFβ) proteins, the glycoprotein hormones, the platelet-derived growth factor-like (PDGF-like) proteins, nerve growth factors (NGF), and the differential screening-selected gene aberrative in neuroblastoma (DAN) family (e.g., cerberus). In turn, the TGFβ superfamily comprises approximately 43 members, subdivided into three subfamilies: the TGFβs, the activins and the bone morphogenetic/growth differentiation factor proteins (BMP/GDF).

The TGF-β superfamily members contain the canonical cystine knot topology. That is, cystine knots are the result of an unusual arrangement of six cysteine residues. The knot consists of bonds between cysteines 1-4, cysteines 2-5, and the intervening sequence forming a ring, through which the disulfide bond between cysteines 3-6 passes. The active forms of these proteins are homodimers or heterodimers. In each case the monomer topology is stabilized by the cysteine knot and additional cysteines contribute to additional intra-chain bonds and/or mediate dimerization with another protein unit. See Kingsley, 1994, Genes Dev. 8:133-146; Lander et al, 2001, Nature 409:860-921.

BMP/GDFs are the most numerous members of the TGF-β protein superfamily. The BMP/GDF subfamily includes, but is not limited to, BMP2, BMP3 (osteogenin), BMP3b (GDF-10), BMP4 (BMP2b), BMP5, BMP6, BMP7 (osteogenic protein-1 or OP1), BMP8 (OP2), BMP8B (OP3), BMP9 (GDF2), BMP10, BMP11 (GDF11), BMP12 (GDF7), BMP13 (GDF6, CDMP2), BMP15 (GDF9), BMP16, GDF1, GDF3, GDF5 (CDMP1; MP52), and GDF8 (myostatin). BMPs are sometimes referred to as Osteogenic Protein (OPs), Growth Differentiation Factors (GDFs), or Cartilage-Derived Morphogenetic Proteins (CDMPs). BMPs are also present in other animal species. Furthermore, there is some allelic variation in BMP sequences among different members of the human population.

BMPs are naturally expressed as pro-proteins comprising a long pro-domain, one or more cleavage sites, and a mature domain. This pro-protein is then processed by the cellular machinery to yield a dimeric mature BMP molecule. The pro-domain is believed to aid in the correct folding and processing of BMPs. Furthermore, in some but not all BMPs, the pro-domain may noncovalently bind the mature domain and may act as a chaperone, as well as an inhibitor (e.g., Thies et al., Growth Factors 18:251-9 (2001)).

BMP signal transduction is initiated when a BMP dimer binds two type I and two type II serine/threonine kinase receptors. Type I receptors include, but are not limited to, ALK-1 (Activin receptor-Like Kinase 1), ALK-2 (also called ActRIa or ActRI), ALK-3 (also called BMPRIa), and ALK-6 (also called BMPRIb). Type II receptors include, but are not limited to, ActRIIa (also called ActRII), ActRIIb, and BMPRII. The human genome contains 12 members of the receptor serine/threonine kinase family, including 7 type I and 5 type II receptors, all of which are involved in TGF-β signaling (Manning et al., Science 298:1912-34 (2002)), the disclosures of which are hereby incorporated by reference). Thus, there are 12 receptors and 43 superfamily members, suggesting that at least some TGF-β superfamily members bind the same receptor(s). Following BMP binding, the type II receptors phosphorylate the type I receptors, the type I receptors phosphorylate members of the Smad family of transcription factors, and the Smads translocate to the nucleus and activate the expression of a number of genes.

BMPs are among the most numerous members of TGF-β superfamily, and control a diverse set of cellular and developmental processes, such as embryonic pattern formation and tissue specification as well as promoting wound healing and repair processes in adult tissues in, among other places, the nervous system and the skeletal system. In fact, BMPs were initially isolated by their ability to induce bone and cartilage formation: BMP signaling is inducible upon bone fracture and related tissue injury, leading to bone regeneration and repair. Given their roles in development and normal wound healing, BMPs hold immense promise for the regeneration and repair of the skeletal system, nervous system, and other tissues where BMP receptors are expressed. This promise would be even greater for BMPs with altered affinity for their receptors and/or improved biological activity relative to the native proteins. The inventors have previously described designer BMPs with altered binding to BMP receptors and with increased activity in various in vitro and in vivo assays. Yet the universe of designer BMPs currently known remains relatively small, and there is an ongoing need in the field for the development of new and novel designer BMPs.

SUMMARY OF THE INVENTION

The present invention addresses this need by providing, in its various aspects, novel designer BMPs based on BMPs 2, 4, 6 and 7, compositions and methods relating to these designer BMPs, and methods of making and using the same. In one aspect, the invention relates to a designer BMP comprising, in various embodiments, an amino acid sequence selected from the group consisting of SEQ ID NOS: 8, 9, 10, 11, 12, 13, 14 and 15. The designer BMP optionally includes one or more mutations not in the Type I, Type II A, or Type II B binding domains; there may be, variously, 1, 2, 3, 4, 5, 6 7, 8, 9, 10 or more such mutations. Alternatively or additionally, the designer BMP exhibits a receptor binding profile which differs from a wild-type BMP, which binding profile includes, one, several or all of the following: binding to the ALK2 receptor with a $K_D$ not greater than about 2 nM; binding to the ALK3 receptor with a $K_D$ not greater than about 2 nM; binding to the ALK6 receptor with a $K_D$ not greater than about 1 nM; binding to the ActRIIA receptor with a $K_D$ not greater than about 2 nM; binding to the ActRIIB receptor with a $K_D$ not greater than about 0.5 nM; and binding to the BMPRIIA receptor with a $K_D$ not greater than about 3.5 nM.

In another aspect, the invention relates to a designer BMP comprising the following mutations relative to SEQ ID NO:1: V33I, P36E, H39A, H44E, P48A, A52N, D53S, H54Y, L55M, S57A, N68H, S69F, V70I, S72P, K73E, insertion of a T following K73, I74V, A77P, V80A, S85N, M89V, L92F, E94D, N95S, E96S, K97N, V99I. In some embodiments, the designer BMP optionally includes one or more mutations not in the Type I, Type II A, or Type II B binding domains; there may be, variously, 1, 2, 3, 4, 5, 6 7, 8, 9, 10 or more such mutations. Alternatively or additionally, the designer BMP exhibits a receptor binding profile which differs from a wild-type BMP, which binding profile includes, one, several or all of the following: binding to the ALK2 receptor with a $K_D$ not greater than about 2 nM; binding to the ALK3 receptor with a $K_D$ not greater than about 2 nM; binding to the ALK6 receptor with a $K_D$ not greater than about 1 nM; binding to the ActRIIA receptor with a $K_D$ not greater than about 2 nM; binding to the ActRIIB receptor with a $K_D$ not greater than about 0.5 nM; and binding to the BMPRIIA receptor with a $K_D$ not greater than about 3.5 nM. The designer BMP may have an amino acid sequence comprising SEQ ID NO:8 in some instances, while in other instances, the designer BMP further comprises the following mutations relative to SEQ ID NO:8: E84K, N86R, A87P, I88M, V90M, F93Y, S96G, S97Q, V99I, L101K, N103D, Y104I, D106N, V108I, G111E, R115S.

In another aspect, the invention relates to a designer BMP comprising the following mutations relative to SEQ ID NO:1: V33I, P36E, H39A, H44E, P48A, A52N, D53S, H54Y, L55M, S57A, N68H, S69F, V70I, S72P, K73E, insertion of a T following K73, I74V, A77P, V80A, E83K, S85R, A86P, I87M, L92Y, E94D, N95G, E96Q, K97N, V98I, V99I, L100K, N102D, Y103I, D105N, V107I, G110E, R114S. In some embodiments, the designer BMP optionally includes one or more mutations not in the Type I, Type IIA, or Type II B binding domains; there may be, variously, 1, 2, 3, 4, 5, 6 7, 8, 9, 10 or more such mutations. Alternatively or additionally, the designer BMP exhibits a receptor binding profile which differs from a wild-type BMP, which binding profile includes, one, several or all of the following: binding to the ALK2 receptor with a $K_D$ not greater than about 2 nM; binding to the ALK3 receptor with a $K_D$ not greater than about 2 nM; binding to the ALK6 receptor with a $K_D$ not greater than about 1 nM; binding to the ActRIIA receptor with a $K_D$ not greater than about 2 nM; binding to the ActRIIB receptor with a $K_D$ not greater than about 0.5 nM; and binding to the BMPRIIA receptor with a $K_D$ not greater than about 3.5 nM. The designer BMP may have an amino acid sequence comprising SEQ ID NO: 9 in some instances.

In yet another aspect, the invention relates to a designer BMP comprising the following mutations relative to SEQ ID NO:2: V35I, P38K, Q41A, H46D, D48E, P50S, A54N, D55A, L57M, S59A, N70H, S71L, V72P, S74P, S75E, insertion of a Y after S75, I76V, A79P, V82A, S87N, M91V, L94F, E96D, Y97N, D98S, K99N, V101I. In some embodiments, the designer BMP optionally includes one or more mutations not in the Type I, Type II A, or Type II B binding domains; there may be, variously, 1, 2, 3, 4, 5, 6 7, 8, 9, 10 or more such mutations. Alternatively or additionally, the designer BMP exhibits a receptor binding profile which differs from a wild-type BMP, which binding profile includes, one, several or all of the following: binding to the ALK2 receptor with a $K_D$ not greater than about 2 nM; binding to the ALK3 receptor with a $K_D$ not greater than about 2 nM; binding to the ALK6 receptor with a $K_D$ not greater than about 1 nM; binding to the ActRIIA receptor with a $K_D$ not greater than about 2 nM; binding to the ActRIIB receptor with a $K_D$ not greater than about 0.5 nM; and binding to the BMPRIIA receptor with a $K_D$ not greater than about 3.5 nM. The designer BMP may have an amino acid sequence comprising SEQ ID NO: 10 in some instances. In other cases, the designer BMP may further include a mutation of K38R relative to SEQ ID NO: 10, and/or may comprise the amino acid sequence of SEQ ID NO: 12.

In yet another aspect, the present invention relates to a designer BMP comprising the following mutations relative to SEQ ID NO:2: V35I, P38K, Q41A, H46D, D48E, P50S, A54N, D55A, L57M, S59A, N70H, S71L, V71M, S74P, S75E, insertion of a Y after S75, I76V, A79P, V82A, E85K, S87R, A88P, I89M, L94Y, E96D, Y97G, D98Q, K99N, V100I, V101OI, L102K, N104D, Y105I, E107N, V109I, G112E, R116S. In some embodiments, the designer BMP optionally includes one or more mutations not in the Type I, Type II A, or Type II B binding domains; there may be, variously, 1, 2, 3, 4, 5, 6 7, 8, 9, 10 or more such mutations. Alternatively or additionally, the designer BMP exhibits a receptor binding profile which differs from a wild-type BMP, which binding profile includes, one, several or all of the following: binding to the ALK2 receptor with a $K_D$ not greater than about 2 nM; binding to the ALK3 receptor with a $K_D$ not greater than about 2 nM; binding to the ALK6 receptor with a $K_D$ not greater than about 1 nM; binding to the ActRIIA receptor with a $K_D$ not greater than about 2 nM; binding to the ActRIIB receptor with a $K_D$ not greater than about 0.5 nM; and binding to the BMPRIIA receptor with a $K_D$ not greater than about 3.5 nM. The designer BMP may have an amino acid sequence comprising SEQ ID NO: 11 in some instances.

In yet another aspect, the present invention relates to a designer BMP comprising the following mutations relative to SEQ ID NO:2: V35I, P38R, Q41A, H46D, D48E, P50S, A54N, D55A, L57M, S59A, N70H, S71L, V72M, S74P, S75E, insertion of a Y after S75, I76V, A79P, V82A, E85K, S87R, A88P, I89M, L94Y, E96D, Y97G, D98Q, K99N, V100I, V101I, L102K, N104D, Y105I, E107N, V109I, G112E, R116S. In some embodiments, the designer BMP optionally includes one or more mutations not in the Type I, Type II A, or Type II B binding domains; there may be, variously, 1, 2, 3, 4, 5, 6 7, 8, 9, 10 or more such mutations. Alternatively or additionally, the designer BMP exhibits a receptor binding profile which differs from a wild-type BMP, which binding profile includes, one, several or all of the following: binding to the ALK2 receptor with a $K_D$ not greater than about 2 nM; binding to the ALK3 receptor with a $K_D$ not greater than about 2 nM; binding to the ALK6 receptor with a $K_D$ not greater than about 1 nM; binding to the ActRIIA receptor with a $K_D$ not greater than about 2 nM; binding to the ActRIIB receptor with a $K_D$ not greater than about 0.5 nM; and binding to the BMPRIIA receptor with a K_D not greater than about 3.5 nM. The designer BMP optionally has an amino acid sequence comprising SEQ ID NO: 13.

In yet another aspect, the present invention relates to a designer BMP comprising the following mutations relative to SEQ ID NO:2: V35I, P38E, Q41A, H46E, D48E, P50A, A54N, D55S, H56Y, L57M, S59A, N70H, S71F, V72I, insertion of a P after N73, S74E, S75T, I76V, A79P, V82A, S87N, M91V, L94F, E96D, Y97S, D98S, K99N, V101I. In some embodiments, the designer BMP optionally includes one or more mutations not in the Type I, Type II A, or Type II B binding domains; there may be, variously, 1, 2, 3, 4, 5, 6 7, 8, 9, 10 or more such mutations. Alternatively or additionally, the designer BMP exhibits a receptor binding profile which differs from a wild-type BMP, which binding profile includes, one, several or all of the following: binding to the ALK2 receptor with a $K_D$ not greater than about 2 nM; binding to the ALK3 receptor with a $K_D$ not greater than about 2 nM; binding to the ALK6 receptor with a $K_D$ not greater than about 1 nM; binding to the ActRIIA receptor with a $K_D$ not greater than about 2 nM; binding to the ActRIIB receptor with a $K_D$ not greater than about 0.5 nM; and binding to the BMPRIIA receptor with a $K_D$ not greater than about 3.5 nM. The designer BMP may have an amino acid sequence comprising SEQ ID NO: 14.

And in yet another aspect, the present invention relates to a designer BMP comprising the following mutations relative to SEQ ID NO: 2: V35I, P38E, Q41A, H46E, D48E, P50A, A54N, D55S, H56Y, L57M, S59A, N70H, S71F, V72I, insertion of a P after N73, S74E, S75T, I76V, A79P, V82A, E85K, S87R, A88P, I89M, L94Y, E96D, Y97G, D98Q, K99N, V100I, V101I, L102K, N104D, Y105I, E107N, V109I, G112E, R116S. In some embodiments, the designer BMP optionally includes one or more mutations not in the Type I, Type II A, or Type II B binding domains; there may be, variously, 1, 2, 3, 4, 5, 6 7, 8, 9, 10 or more such mutations. Alternatively or additionally, the designer BMP exhibits a receptor binding profile which differs from a wild-type BMP, which binding profile includes, one, several or all of the following: binding to the ALK2 receptor with a $K_D$ not greater than about 2 nM; binding to the ALK3 receptor with a $K_D$ not greater than about 2 nM; binding to the ALK6 receptor with a $K_D$ not greater than about 1 nM; binding to the ActRIIA receptor with a $K_D$ not greater than about 2 nM; binding to the ActRIIB receptor with a $K_D$ not greater than about 0.5 nM; and binding to the BMPRIIA receptor with a $K_D$ not greater than about 3.5 nM. The designer BMP may have an amino acid sequence comprising SEQ ID NO: 15.

The invention further includes methods of producing a designer BMP proteins of the types described above. The methods generally include introducing a nucleic acid encoding the protein into a host cell, culturing the cell under conditions where the protein is produced, and purifying the protein.

In various aspects the invention relates to a nucleic acid that encodes an amino acid sequence selected from the group consisting of SEQ ID NOS: 8-15, or specifically encodes. SEQ ID NO:8, SEQ ID NO:9, SEQ ID NO:10, SEQ ID NO:11, SEQ ID NO:12, SEQ ID NO:13, SEQ ID NO:14, and/or SEQ ID NO:15. The nucleic acid can be incorporated into any suitable expression vector, which in turn can be introduced into a cell for expression and harvesting, as discussed below.

The invention also includes methods of treating a bone disease associated with bone loss in a patient in need thereof. In one aspect, the method includes administering a therapeutically effective amount of a designer BMP protein as described above, thereby treating bone disease in the patient. In various embodiments, the designer BMP protein includes an amino acid sequence selected from the group consisting of SEQ ID NOS: 8-15, or specifically SEQ ID NO:8, SEQ ID NO:9, SEQ ID NO:10, SEQ ID NO:11, SEQ ID NO:12, SEQ ID NO:13, SEQ ID NO:14, and/or SEQ ID NO:15.

The invention includes a method of treating fibrosis in a patient in need thereof. In one aspect, the invention relates to a method which includes administering a therapeutically effective amount of a designer BMP protein as described above, thereby treating fibrosis. In various embodiments, the designer BMP protein includes an amino acid sequence selected from the group consisting of SEQ ID NOS: 8-15, or specifically SEQ ID NO:8, SEQ ID NO:9, SEQ ID NO:10, SEQ ID NO:11, SEQ ID NO:12, SEQ ID NO:13, SEQ ID NO:14, and/or SEQ ID NO:15.

Additionally, the invention includes a method of inducing bone formation in a tissue. In this aspect, the method comprises contacting the tissue with a designer BMP protein as described above, thereby inducing bone formation in said tissue. In various embodiments, the designer BMP protein is amino acid sequence selected from the group consisting of SEQ ID NOS: 8-15, or specifically SEQ ID NO:8, SEQ ID NO:9, SEQ ID NO:10, SEQ ID NO:11, SEQ ID NO:12, SEQ ID NO:13, SEQ ID NO:14, and/or SEQ ID NO:15.

Finally, one aspect of the invention relates to a kit for treating a patient, which includes a designer BMP as described above. In various embodiments, the designer BMP protein includes an amino acid sequence selected from the group consisting of SEQ ID NOS: 8-15, or specifically SEQ ID NO:8, SEQ ID NO:9, SEQ ID NO:10, SEQ ID NO:11, SEQ ID NO:12, SEQ ID NO:13, SEQ ID NO:14, and/or SEQ ID NO:15. Kits of the present invention optionally or additionally include a fluid for diluting the designer BMP, thereby creating a designer BMP solution, and/or a medical instrument or an implant material for use with the designer BMP solution.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

Figure 1:
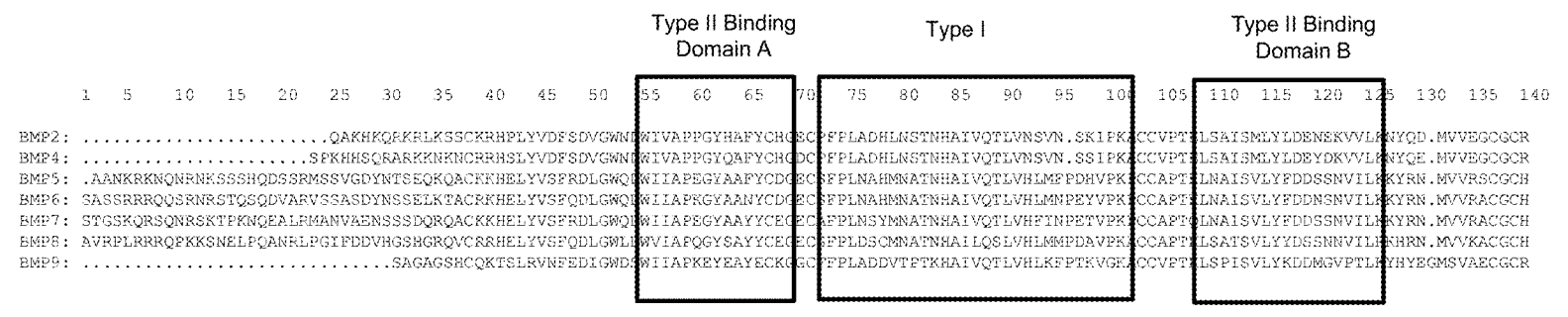

FIG. 1 is a diagram showing the alignment of various wild type and designer BMP amino acid sequences and indicating (by being within a box) the regions of these proteins potentially involved in type I and type II receptor interactions. FIG. 1 shows the amino acid sequence alignment of wild type BMP2 (SEQ ID NO: 1), BMP4 (SEQ ID NO: 2), BMP5 (SEQ ID NO: 3), BMP6 (SEQ ID NO: 4), BMP7 (SEQ ID NO: 5), BMP8 (SEQ ID NO: 6) and BMP9 (SEQ ID NO: 7).

FIG. 3, comprising panels A and B, is an diagram of a structural model showing the position of the histidine doorstop (H54) in human BMP2 produced in Chinese Hamster Ovary (CHO) (FIG. 3A) and E. coli cells (FIG. 3B).

FIG. 4, comprising panels A and B, is a diagram illustrating the location of the glycan tether and potential histidine (His) doorstop.

FIG. 5, comprising panels A-D, shows various steps in the process for purification of BMPs and designer BMPs.

DETAILED DESCRIPTION OF THE INVENTION

Figure 2:
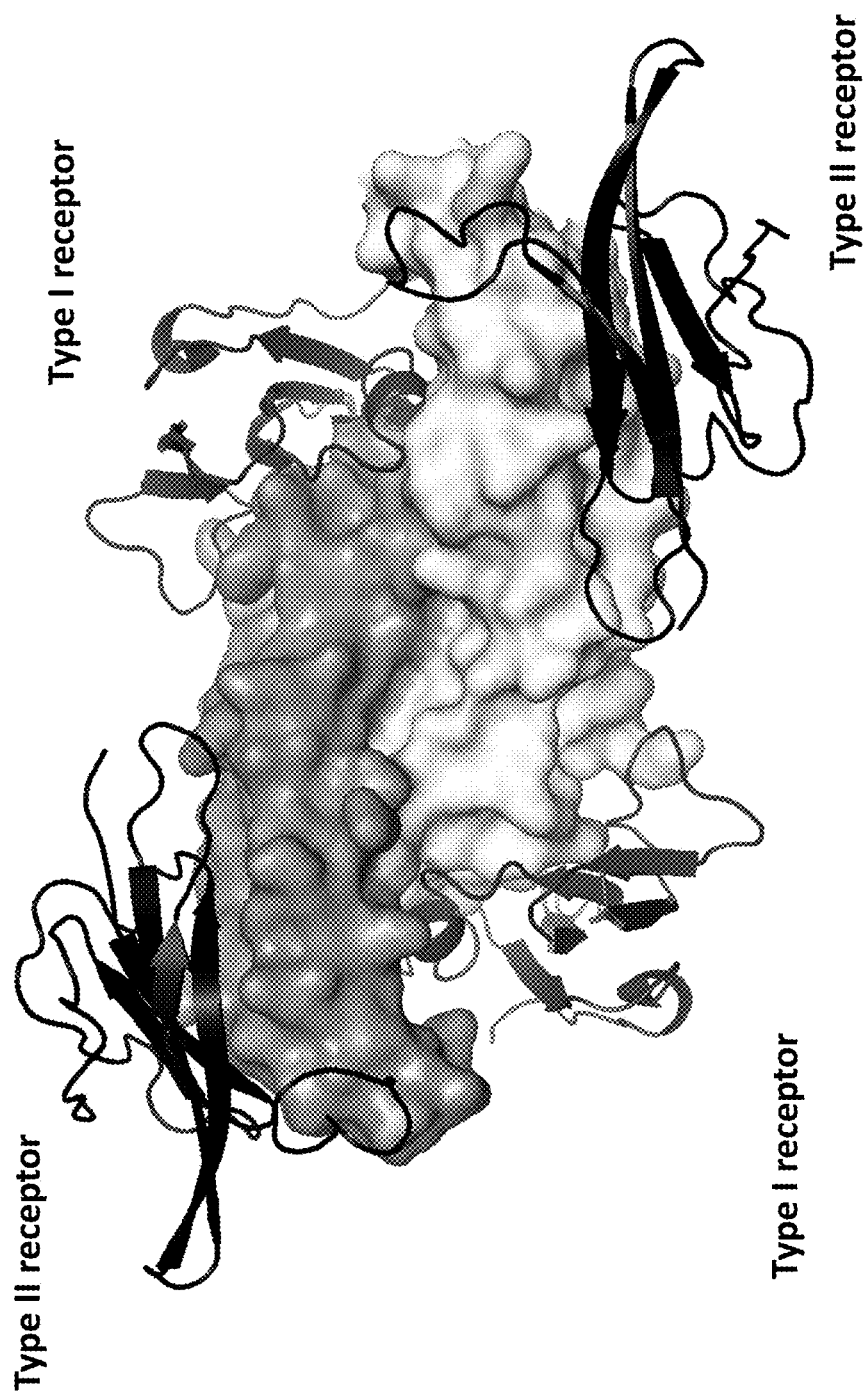
FIG. 2 is an illustration of a structural model showing a wild type BMP2 homodimer binding to two type I and two type II BMP receptors.
Figures 4A, 4B:
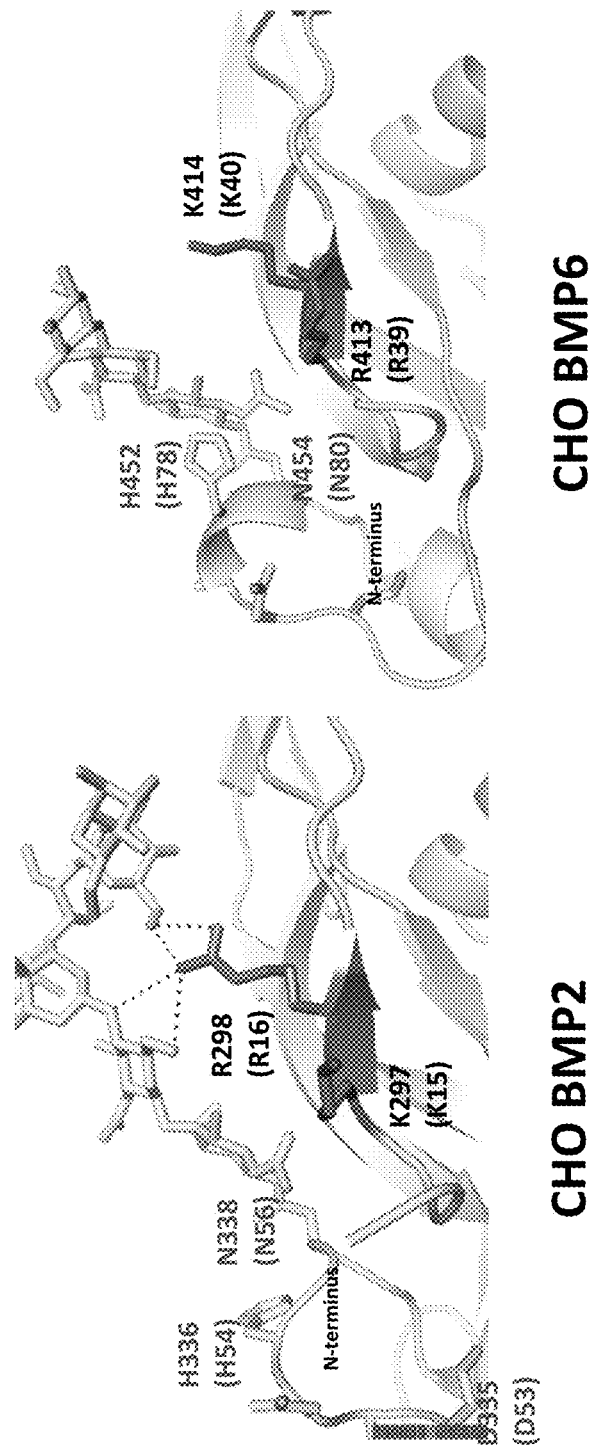
FIG. 4A shows the glycan tether (N-linked glycan at N56) and histidine 54, in the non-doorstop orientation, as well as the interaction of the glycan tether with R16 all in CHO-produced BMP2.
FIG. 4B shows the glycan tether (N-linked glycan at N80) and the histidine in the non-doorstop configuration at H78 in BMP6, as well as the R39 corresponding to R16 in BMP2.
Figure 5A:
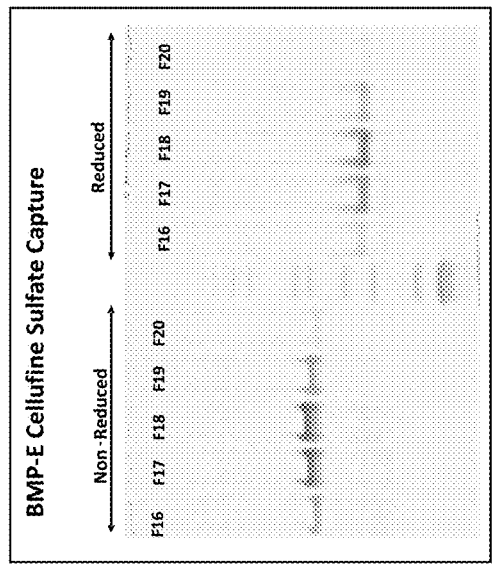
FIG. 5A shows a chromatogram showing gradient elution of BMPs using a cellufine sulfate column.
Figure 5B:
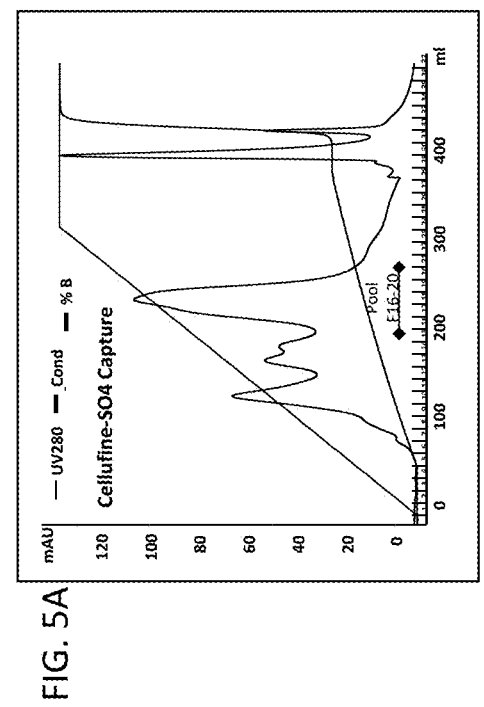
FIG. 5B is an image of a Coomassie stained SDS-PAGE (non-reduced on the left and reduced on the right side) gel containing samples of fractions from the cellufine sulfate column step.
Figure 5C:
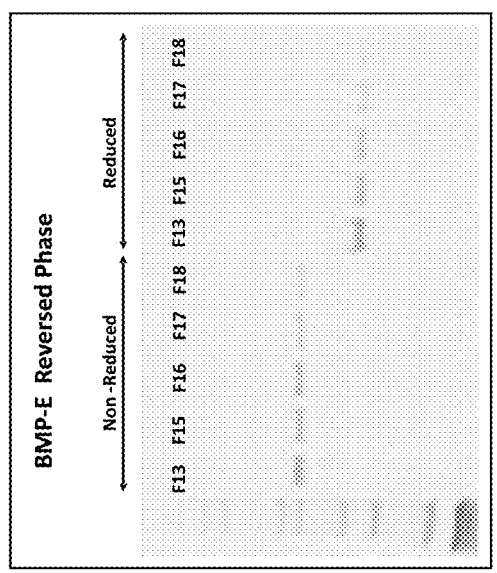
FIG. 5C shows a chromatogram showing the profile from preparative reversed phase purification step.
Figure 5D:
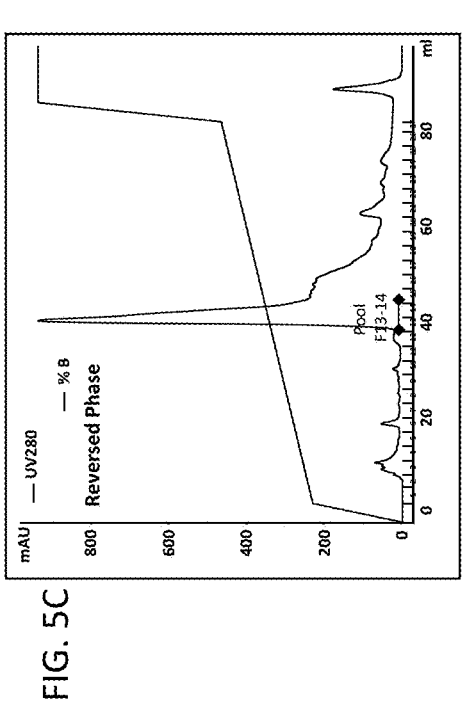
FIG. 5D is an image of a Coomassie stained SDS-PAGE (non-reduced on the left and reduced on the right) gel of BMP containing samples of the fractions obtained by the preparative reversed phase purification step.

This invention relates a "designer" bone morphogenetic protein, referred to herein as "designer BMP," "designer osteogenic protein" and "designer protein." The designer BMPs of the invention may correspond to the amino acid sequences of wild type unmodified BMP, such as, but not limited to, BMP2 (SEQ ID NO:1), BMP4 (SEQ ID NO:2), BMPS (SEQ ID NO:3), BMP6 (SEQ ID NO:4), BMP7 (SEQ ID NO:5), BMP8 (SEQ ID NO:6), and BMP9 (SEQ ID NO:7). In particular embodiments, the designer BMPs show altered binding to a type I and/or type II BMP receptor when compared to its corresponding wild type BMP. In further embodiments, the designer BMP may be modified to have altered half-life, immunogenicity, or any pharmacokinetic/pharmacodynamic (PK/PD) parameter when compared to its corresponding BMP.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to methods well known in the art and as described in various general and more specific references that are cited and discussed throughout the present specification unless otherwise indicated. Such references include, e.g., Sambrook and Russell, *Molecular Cloning, A Laboratory Approach*, Cold Spring Harbor Press, Cold Spring Harbor, N.Y. (2001), Ausubel et al., *Current Protocols in Molecular Biology*, John Wiley & Sons, NY (2002), and Harlow and Lane, *Antibodies: A Laboratory Manual*, Cold Spring Harbor Laboratory Press, Cold Spring Harbor, N.Y. (1990), which are incorporated herein by reference. Enzymatic reactions and purification techniques are performed according to manufacturers specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

In this application, the use of "or" means "and/or" unless stated otherwise.

Conventional notation is used herein to portray polypeptide sequences: the left-hand end of a polypeptide sequence is the amino-terminus; the right-hand end of a polypeptide sequence is the carboxyl-terminus. As used herein, the twenty conventional amino acids and their abbreviations follow conventional usage. See *Immunology—A Synthesis* (2nd Edition, E. S. Golub and D. R. Gren, Eds., Sinauer Associates, Sunderland, Mass. (1991)), which is incorporated herein by reference. As used herein, amino acids are represented by the full name thereof, by the three letter code corresponding thereto, or by the one-letter code corresponding thereto, as indicated as follows:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, *Methods Mol. Biol.* 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6)

acidic side chains: aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., *Science* 256:1443-1445 (1992), herein incorporated by reference. A "moderately conservative" replacement is any change having a nonnegative value in the PAM250 log-likelihood matrix.

Preferred amino acid substitutions are those which: (1) reduce susceptibility to proteolysis, (2) reduce susceptibility to oxidation, (3) alter binding affinity for forming protein complexes, and (4) confer or modify other physicochemical or functional properties of such analogs. Analogs comprising substitutions, deletions, and/or insertions can include various muteins of a sequence other than the specified peptide sequence. For example, single or multiple amino acid substitutions (preferably conservative amino acid substitutions) may be made in the specified sequence (preferably in the portion of the polypeptide outside the domain(s) forming intermolecular contacts, e.g., outside of the CDRs or the type I or type II receptor binding sites). A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et al., *Nature* 354: 105 (1991), which are each incorporated herein by reference.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This also includes nucleic acids containing modified bases, for example, thio-uracil, thio-guanine, and fluoro-uracil, or containing carbohydrate, or lipids.

In the context of a nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence.

By "designer BMP nucleic acids," and grammatical equivalents herein is meant nucleic acids that encode designer BMPs.

The terms "protein" and "polypeptide" are used interchangeably herein. These terms refer to a sequential chain of amino acids linked together via peptide bonds. The terms include one or more proteins that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of multiple polypeptides that physically associate with one another, the term "protein" as used herein refers to the multiple polypeptides that are physically coupled and function together as the discrete unit. A protein to be expressed according to the present invention can be a protein therapeutic. A protein therapeutic is a protein that has a biological effect on a region in the body on which it acts or on a region of the body on which it remotely acts via intermediates. Examples of protein therapeutics are discussed in more detail below.

"Designer BMP," as the term is used herein, relates to a BMP protein comprising at least one amino acid mutation compared to a corresponding wild type BMP without the mutation, wherein the designer BMP has detectably altered binding for at least a type I receptor and/or at least one type II receptor compared with the binding of the corresponding wild type BMP for the type I and/or type II receptor.

By "corresponding wild type protein" it is meant the wild type version of the designer BMP prior to the introduction of any mutations. For example, if the designer BMP is a designer BMP2, the corresponding wild-type BMP is wild-type BMP2. Thus, in one embodiment, design of a designer BMP can, but need not, begin with a wild type BMP sequence wherein mutations (e.g., amino acid substitutions, deletions and/or insertion) are introduced into the wild type sequence. Therefore, the designer BMP can correspond with a wild type BMP, and the locations of the mutations can be said, for instance, to correspond with, be relative to and/or be respective with the amino acid sequence of the wild type corresponding or "reference" BMP sequence.

The proteins of the present invention include fragments, derivatives, analogs, or variants of the polypeptides described herein, and any combination thereof. The terms "fragment," "variant," "derivative" and "analog" when referring to proteins of the present invention include any proteins which retain at least some of the functional properties of the protein from which it was derived.

By the term "fragment" as used herein refers to a polypeptide and is defined as any discrete portion of a given polypeptide that is unique to or characteristic of that polypeptide. The term as used herein also refers to any discrete portion of a given polypeptide that retains at least a fraction of the activity of the full-length polypeptide. In certain embodiments, the fraction of activity retained is at least 10% of the activity of the full-length polypeptide. In certain embodiments, the fraction of activity retained is at least 20%, 30%, 40%, 50%, 60%, 70%, 80% or 90% of the activity of the full-length polypeptide. In certain embodiments, the fraction of activity retained is at least 95%, 96%, 97%, 98% or 99% of the activity of the full-length polypeptide. In certain embodiments, the fraction of activity retained is 100% or more of the activity of the full-length polypeptide. Alternatively or additionally, the term as used herein also refers to any portion of a given polypeptide that includes at least an established sequence element found in the full-length polypeptide. In some embodiments, the sequence element spans at least about 4-5, 10, 15, 20, 25, 30, 35, 40, 45, 50 or more amino acids of the full-length polypeptide. Fragments of proteins of the present invention include proteolytic fragments, as well as deletion fragments.

Variants of the proteins of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant proteins may comprise conservative or non-conservative amino acid substitutions, deletions or additions.

The proteins of the invention include proteins having one or more residues chemically derivatized by reaction of a functional side group. Also included as proteins of the invention are polypeptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

"Recombinantly expressed polypeptide" and "recombinant polypeptide" as used herein refer to a polypeptide expressed from a host cell that has been manipulated to express that polypeptide. In certain embodiments, the host cell is a mammalian cell. In certain embodiments, this manipulation may comprise one or more genetic modifications. For example, the host cells may be genetically modified by the introduction of one or more heterologous genes encoding the polypeptide to be expressed. The heterologous recombinantly expressed polypeptide can be identical or similar to polypeptides that are normally expressed in the host cell. The heterologous recombinantly expressed polypeptide can also be foreign to the host cell, e.g. heterologous to polypeptides normally expressed in the host cell. In certain embodiments, the heterologous recombinantly expressed polypeptide is chimeric. For example, portions of a polypeptide may contain amino acid sequences that are identical or similar to polypeptides normally expressed in the host cell, while other portions contain amino acid sequences that are foreign to the host cell. Additionally or alternatively, a polypeptide may contain amino acid sequences from two or more different polypeptides that are both normally expressed in the host cell. Furthermore, a polypeptide may contain amino acid sequences from two or more polypeptides that are both foreign to the host cell. In some embodiments, the host cell is genetically modified by the activation or upregulation of one or more endogenous genes.

Calculations of homology or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a typical embodiment, the length of a reference sequence aligned for comparison purposes is at least 30%, at least 40%, at least 50% or 60%, or at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino acid or nucleic acid sequence). The percent identity between the two sequences is a function of the number of identical positions shared by the sequences (i.e., % homology=# of identical positions/total # of positions×100). The determination of percent homology between two sequences can be accomplished using a mathematical algorithm. A preferred, non-limiting example of a mathematical algorithm utilized for the comparison of two sequences is the algorithm of Karlin et al., Proc Natl Acad Sci USA 87:2264-8 (1990), modified as in Karlin et al., Proc Natl Acad Sci USA 90:5873-7 (1993). Such an algorithm is incorporated into the NBLAST and XBLAST programs of Altschul et al., J Mol Biol 215:403-10 (1990). BLAST nucleotide searches can be performed with the NBLAST program, score=100, wordlength=12.

BLAST protein searches can be performed with the XBLAST program, score=50, wordlength=3. To obtain gapped alignments for comparison purposes, Gapped BLAST can be utilized as described in Altschul et al., Nucleic Acids Res 25:3389-402 (1997). When utilizing BLAST and Gapped BLAST programs, the default parameters of the respective programs (e.g., XBLAST and NBLAST) can be used.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman-Wunsch algorithm (Needleman et al., J Mol Biol 48:443-53 (1970)) which has been incorporated into the GAP program in the GCG software package (available on at gcg.com), using either a Blossum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (available on the internet at gcg.com), using a NWSgapdna.CMP matrix and a gap weight of 40, 50, 60, 70, or 80 and a length weight of 1, 2, 3, 4, 5, or 6. One typical set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Myers and W. Miller (Myers et al., Comput Appl Biosci 4:11-7 (1988)) which has been incorporated into the ALIGN program (version 2.0), using a PAM120 weight residue table, a gap length penalty of 12 and a gap penalty of 4.

"Instructional material," as that term is used herein, includes a publication, a recording, a diagram, or any other medium of expression which can be used to communicate the usefulness of the compound, combination, and/or composition of the invention in the kit for affecting, alleviating or treating the various diseases or disorders recited herein. Optionally, or alternately, the instructional material can describe one or more methods of alleviating the diseases or disorders in a cell, a tissue, or a mammal, including as disclosed elsewhere herein.

The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively.

Except when noted, the terms "patient" or "subject" are used interchangeably and refer to mammals such as human patients and non-human primates, as well as veterinary subjects such as rabbits, rats, and mice, and other animals. Preferably, patient refers to a human.

"Effective amount", or "therapeutically effective amount," as the terms are used interchangeably herein, is an amount that when administered to a tissue or a mammal, preferably a human, mediates a detectable therapeutic response compared to the response detected in the absence of the compound. A therapeutic response, such as, but not limited to, inhibition of and/or decreased fibrosis, increased bone mass or bone density, and the like, can be readily assessed by a plethora of art-recognized methods, including, e.g., such methods as disclosed herein.

The skilled artisan would understand that the effective amount of the compound or composition administered herein varies and can be readily determined based on a number of factors such as the disease or condition being treated, the stage of the disease, the age and health and physical condition of the mammal being treated, the severity of the disease, the particular compound being administered, and the like As used herein, to "treat" means reducing the frequency with which symptoms of a disease (e.g., decreased bone density, fracture, fibrosis, and the like) are experienced by a patient. The term includes the administration of the compounds or agents of the present invention to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

By the phrase "specifically binds," as used herein, is meant a compound, e.g., a protein, a nucleic acid, an antibody, and the like, which recognizes and binds a specific molecule, but does not substantially recognize or bind other molecules in a sample. For instance, an BMP protein, an antibody or a peptide inhibitor which recognizes and binds a cognate receptor (e.g., a BMP type I or type II receptor, an antibody that binds with its cognate antigen, and the like) in a sample, but does not substantially recognize or bind other molecules in the sample. Thus, under designated assay conditions, the specified binding moiety (e.g., a BMP or a receptor binding fragment thereof) binds preferentially to a particular target molecule and does not bind in a significant amount to other components present in a test sample. A variety of assay formats may be used to select an antibody that specifically binds a molecule of interest. For example, solid-phase ELISA immunoassay, immunoprecipitation, BIAcore, FACS, Octet, and Western blot analysis are among many assays that may be used to identify a BMP that specifically reacts with a BMP receptor. Typically, a specific or selective reaction will be at least twice background signal or noise, more preferably, at least five-fold greater than background signal or noise, and more typically, more than 10 times background, even more specifically, a BMP is said to "specifically bind" a BMP receptor when the equilibrium dissociation constant ($K_D$) is ≤100 µM, more preferably ≤10 µM, even more preferably ≤1 µM, yet more preferably ≤100 nM and most preferably ≤10 nM.

The term "$K_D$" refers to the equilibrium dissociation constant of a particular ligand-receptor interaction.

"Binding affinity" generally refers to the strength of the sum total of noncovalent interactions between a binding site of a molecule (e.g., a BMP ligand) and its binding partner (e.g., a BMP type I or type II receptor). Unless indicated otherwise, as used herein, "binding affinity" refers to intrinsic binding affinity which reflects a 1:1 interaction between members of a binding pair (e.g., BMP and its cognate receptor). The affinity of a molecule X for its partner Y can generally be represented by the dissociation constant (Kd).

Affinity can be measured by common methods known in the art, including those described herein. Low-affinity BMPs generally bind a receptor slowly and tend to dissociate readily, whereas high-affinity BMPs generally bind a receptor faster and tend to remain bound longer. A variety of methods of measuring binding affinity are known in the art, any of which can be used for purposes of the present invention. Specific illustrative embodiments are described elsewhere herein.

The term "$k_{on}$", as used herein is intended to refer to the association or on rate constant, or specific reaction rate, of the forward, or complex-forming, reaction, measured in units: $M^{-1} sec^{-1}$.

The term "$k_{off}$", as used herein, is intended to refer to the dissociation or off rate constant, or specific reaction rate, for dissociation of an antibody from the antibody/antigen complex, measured in units: $sec^{-1}$.

The term "$K_d$", as used herein, is intended to refer to the dissociation constant of a particular antibody-antigen interaction. It is calculated by the formula:

$$k_{off}/k_{on}=K_d$$

The term "altered binding" as used herein means the designer BMP comprises a different binding specificity for at least a type I receptor and/or a type II receptor when compared with the binding of a corresponding wild type BMP to the same type I and/or type II receptor. The designer BMP may bind with greater or lesser affinity with the receptor compared to the binding of the wild type BMP to that receptor. For instance, if the wild type BMP bound a certain type I receptor with a certain binding affinity, the corresponding designer BMP binds that receptor with greater or lesser affinity compared with the wild type BMP. It may even be that the designer BMP will specifically bind a receptor that the wild type BMP did not detectably bind and vice-a-versa where the designer BMP will no longer detectably bind a receptor that the wild type BMP binds. Thus, altered binding encompasses any detectable change in binding by a designer BMP to a type I or type II receptor compared with the binding of that receptor by the corresponding wild type BMP. It may be that the designer BMP has a greater or lesser $k_{on}$ value compared with the $k_{on}$ value for a corresponding wild type BMP and/or the designer BMP has a greater or lesser $k_{off}$ value compared with the $k_{off}$ value of the corresponding wild type BMP such that the Kd of the designer BMP is greater or lesser than the Kd of a corresponding wild type BMP for the same BMP receptor. Thus, any difference in a binding characteristic and/or affinity value between a designer BMP and a corresponding wild type BMP are encompassed by the term "altered binding" as used herein.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden, and Piscataway, N.J.). For further descriptions, see, e.g., Johnsson, et al., *Ann. Biol. Clin.* 51: 19-26 (1993); Johnsson, et al., *Biotechniques* 11: 620-627 (1991); Johnsson, et al., *J. Mol. Recognit.* 8: 125-131 (1995); and Johnnson, et al., *Anal. Biochem.* 198: 268-277 (1991).

As used herein, "substantially pure" means an object species is the predominant species present (i.e., on a molar basis it is more abundant than any other individual species in the composition), and preferably a substantially purified fraction is a composition wherein the object species (e.g., a designer BMP) comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

DESCRIPTION

Bone Morphogenetic Proteins (BMPs)

As stated above, BMPs are members of the TGF-β protein superfamily all of which are characterized by six-conserved cysteine residues (Lander et al, (2001) Nature, 409:860-921. The BMP/GDF subfamily includes, but is not limited to, BMP2, BMP3 (osteogenin) (see, e.g., U.S. Pat. No. 6,177,406), BMP3b (GDF-10) (see, e.g., U.S. Pat. No. 6,204,047), BMP4 (BMP2b) (see, e.g., U.S. Pat. No. 6,245,889), BMP5 (see, e.g., U.S. Pat. No. 5,543,394), BMP6 (see, e.g., U.S. Pat. No. 6,613,744), BMP7 (osteogenic protein-1 or OP1) (see, e.g., U.S. Pat. No. 5,141,905), BMP8 (0P2) (see, e.g., U.S. Pat. No. 5,688,678), BMP8B (0P3) (see, e.g., U.S. Pat. No. 5,854,071), BMP9 (GDF2) (see, e.g., U.S. Pat. No. 6,287,816), BMP10 (see, e.g., U.S. Pat. No. 5,703,043), BMP11 (GDF11) (see, e.g., U.S. Pat. No. 6,437,111), BMP12 (GDF7) (see, e.g., U.S. Pat. No. 6,027,919), BMP13 (GDF6, CDMP2) (see, e.g., U.S. Pat. No. 6,027,919), BMP15 (GDF9) (see, e.g., U.S. Pat. No. 6,034,229), BMP16 (see, e.g., U.S. Pat. No. 6,331,612), GDF1 (see, e.g., US Application No. 2004/0039162), GDF3 (see, e.g., U.S. Pat. No. 6,025,475), GDF5 (CDMP1; MP52) (see, e.g., U.S. Pat. No. 5,994,094), and GDF8 (myostatin) (see, e.g., U.S. Pat. No. 5,827,733).

BMPs specifically bind their cognate receptors, which include Type I receptors: ALK-I, ALK-2 (also called ActRIa or ActRI), ALK-3 (also called BMPRIa), and ALK-6 (also called BMPRIb); and Type II receptors: ActRIIa (also called ActRII), ActRIIb, and BMPRII. The BMP-receptor binding interactions have been studied extensively, and the binding specificities of each wild type BMP for each type I and/or type II receptor is generally known in the art and are shown in Table 1. See, e.g., Nickel et al., *Cytokine Growth Factor Rev* 20:367-77 (2009); Heinecke et al., *BMC Biol* 7:59 (2009).

TABLE 1

|  | ALK 1 | ALK 2 | ALK 3 | ALK 6 | ACTIIA | ACTIIB | BMPRII |
|---|---|---|---|---|---|---|---|
| BMP-2 | No Binding | No Binding | ++++ | ++++ | ++ | +++ | ++ |
| BMP-4 | No Binding | No Binding | ++++ | ++++ | ++ | ++ | ++ |
| BMP-6 | No Binding | No Binding | ++ | ++ | ++++ | ++++ | ++++ |
| BMP-7 | No Binding | No Binding | ++ | ++ | ++++ | ++++ | ++++ |
| BMP-9 | +++++ | No Binding | No Binding | No Binding | ++ | +++ | ++++ |

Designer Bone Morphogenetic Proteins with Improved Osteogenic Activity

The present invention is based in part on the understanding that each BMP dimer binds to four BMP receptors: two type I receptors and two type II receptors. The specificities of each BMP for each receptor are known in the art as shown above in Table 1. Also, the receptor binding regions of various BMPs that mediate binding of the BMP for each receptor have been mapped and are shown in Table 2. For instance, it is well established that wild type BMP2 and BMP4 bind type I BMP receptors Alk-3 and ALK-6 with high affinity and bind type II BMP receptors with lower affinity. On the other hand, wild type BMP6 and BMP7 are known to have bind type II receptors ActrIIA, ActrIIB, and BMPRII with high affinity but bind type I receptors with lower affinity than they do to type II. It is believed that the differing cellular responses from the approximately forty-three TGFβ superfamily members signaling through interaction with approximately twelve receptors is believed to be due to each ligand utilizing a specific repertoire of receptors with which it binds with differing affinities. The type I and II binding domains are described in Table 2.

TABLE 2

| BMP | Type II domain A amino acids | Type I domain amino acids | Type II domain B amino acids |
|---|---|---|---|
| BMP2 (SEQ ID NO 1) | 31-44 | 48-76 | 83-100 |
| BMP4 (SEQ ID NO: 2) | 33-46 | 50-78 | 85-102 |
| BMP5 (SEQ ID NO: 3) | 54-67 | 71-100 | 107-120 |
| BMP6 (SEQ ID NO: 4) | 55-69 | 73-102 | 108-126 |

TABLE 2-continued

| BMP | Type II domain A amino acids | Type I domain amino acids | Type II domain B amino acids |
|---|---|---|---|
| BMP7 (SEQ ID NO: 5) | 55-69 | 73-102 | 108-126 |
| BMP8 (SEQ ID NO: 6) | 55-69 | 73-102 | 108-126 |
| BMP9 (SEQ ID NO: 7) | 25-39 | 42-71 | 78-96 |

Rational Amino Acid Substitution to Alter Receptor Binding of Designer BMPs

It is well known in the art that wild type BMP2 shows a relatively high affinity for type I receptors, while wild type BMP6 shows a high affinity for type II receptors. It is further known in the art that heterodimers of wild type BMP2 and BMP6 bind to both type I and type II receptors with relatively high affinity each BMP apparently providing the higher affinity binding site for each receptor. See Table 3, below. The BMP2/6 heterodimers are known to be more active that BMP2 or BMP6 alone or as homodimers, in both in vitro and in vivo bone formation assays. Table 3 shows an example of BMP2 and BMP6 binding affinities to type I and II receptors.

TABLE 3

| | Type I | | Type II | |
|---|---|---|---|---|
| Ligand | ALK3 $K_D$ (nM) | ALK6 $K_D$ (nM) | ActRIIA $K_D$ (nM) | ActRIIB $K_D$ (nM) |
| BMP2 | 0.69 | 0.17 | 141 | 42 |
| BMP6 | 150 | 102 | 0.73 | 2.0 |
| BMP2/6 | 1.67 | 0.43 | 2.56 | 1.15 |

Accordingly, it is an object of the invention to provide designer BMPs with improved binding to type I and/or type II receptors, including (without limitation) binding that mimics, and preferably improves upon, the binding of BMP heterodimers. As shown in FIG. 1 and Table 2, each BMP comprises three binding sites that contribute to receptor binding. From N- to C-terminus, each BMP comprises a type II receptor binding site A, a type I receptor binding site, and a second type II receptor binding site B. Although an exemplary alignment of wild type BMP2, BMP4, BMP5, BMP6, BMP7, BMP8, and BMP9 is illustrated in FIG. 1, the skilled artisan will appreciate that there are well-known alignments providing the relative positioning of various amino acids among the members of the TGBβ superfamily. Such alignments are provided, among others, in International Publication Nos. WO 2009/086131 (e.g., FIGS. 15-17, FIG. 31A), WO 2008/051526 (FIGS. 9-12), WO 2005/118636 (FIG. 6), WO 2005/118635, WO 2005/113585 (FIG. 3), WO 2001/92298 (FIG. 6A-6C), Kirsch et al., *EMBO J.* 19:3314-3324 (2000) (FIG. 1), US Patent Application Publication No., 2007/0293425 (FIG. 6), Groppe et al., *Nature* 420:636-642 (2002), Nickel et al., *J. Bone Joint Surg. Am.* 83:7-14 (2001), and Weber et al., *BMC Structural Biol.* 7:6 (2007). Thus, using protein sequence alignment algorithms and tools well-known in the art, including the alignments of the amino acid sequences of the various TGFβ superfamily members, as well as the disclosure provided herein, the corresponding amino acid in one BMP/GDF protein relative to the amino acid at any position in another BMP/GDF protein can be determined. In one embodiment, the corresponding amino acid residues in BMP-2, BMP-4, BMP-5, BMP-6, BMP-7, BMP-8 and BMP-9 are shown (see, e.g., FIG. 1).

Designer BMPs according to the present invention generally include mutations in the type I binding domain and/or the type II binding domain, wherein the mutations confer altered binding to a type I or type II BMP receptor. In some embodiments, the designer BMP comprises one or more mutations in both a type I binding domain and a first (binding domain A) and/or second (binding domain B) type II binding domain. In other embodiments, the designer BMP comprises one or more mutations in both type II binding domains. In other embodiments, the designer BMP comprises one or more mutations in the first type II binding domain, in the second type II binding domain, and in the type I binding domain. In some embodiments, the designer BMP comprises one or more mutations in the type I binding domain.

The mutations described above are, in preferred embodiments, generated by one or more "swaps" between corresponding domains of different TGFβ superfamily members, creating chimeric designer BMPs. For instance, in Berasi et al., swaps between BMP-2 and BMP-6 are used to create various designer BMPs. In the present disclosure, the teachings of Berasi et al. are expanded to include swaps between BMP-2, 4, 6 and 7, though the skilled artisan will appreciate that other swaps are possible among these and other TGFβ superfamily members.

As non-limiting examples, BMP-GE27 (SEQ ID NO:8) includes swaps of the Type I and Type II A and B domains of BMP-7 into BMP-2, resulting in a BMP-2/7 chimera. Similarly, BMP-GE46 (SEQ ID NO:10) and BMP-GE47 (SEQ ID NO: 14) include Type I and Type II A and B domains of BMPs 6 and 7 (respectively) into BMP-4.

In addition to the mutation strategies above, the inventors discovered (and disclosed Berasi et al.) that a separate swap of the C-terminal region of activin-A into a designer BMPs results in a designer BMP with extremely high affinity for the ActRIIB receptor, such that the resulting molecules are functionally indifferent to Noggin, binding BMP receptors even in the presence of high concentrations of Noggin. Accordingly, the invention includes, in certain embodiments, dBMPs which incorporate one or more C-terminal mutations point mutations and/or "swaps" such as BMP-GE27-NR (SEQ ID NO. 9), BMP-GE46-NR (SEQ ID NO:11), BMP-GER46-NR (SEQ ID NO:13) or BMP-GE47-NR (SEQ ID NO:15).

In some embodiments, the mutations improve binding to a type I receptor. In other embodiments, the mutations improve binding to a type II receptor. In other embodiments, the mutations decrease binding to a type I or type II receptors. In some embodiments, the mutations create or destroy a glycan tether as more fully set forth below. In some embodiments, the mutations create or destroy a His doorstop as more fully set forth below.

Because BMPs are so well characterized and understood in the art, it would be understood, once provided with the disclosure provided herein, the location of possible mutations that can be made that do not further affect the activity of the designer BMPs would be understood. Accordingly, the designer BMPs of the invention encompass variant BMPs which differ from a corresponding wild type or designer BMP in that it contains additional insertions, deletions, or substitutions which do not affect the receptor binding affinity of the variant BMPs. In some non-limiting embodiments, those of skill in the art would understand that the cysteines involved in cysteine knot formation and amino acids involved in receptor interactions should not be mutated or should be changed with conservative substitutions, while other amino acids may be more freely substituted, inserted, or deleted without adversely affecting biological activity of the designer BMP.

It should be noted that unless otherwise stated, all positional numbering of designed or modified BMPs is based on the sequences of the mature native BMPs. Designer BMPs are characterized by the predetermined nature of the variation, a feature that sets them apart from naturally occurring allelic or interspecies variation of the BMP sequence. Variants of designer BMPs must retain at least 50% of the activity of the corresponding wild type or designer BMP activity in one or more cell types, as determined using an appropriate assay described below. Variants that retain at least 75%, 80%, 85%, 90% or 95% of wild type activity are more preferred, and variants that are more active than wild type are especially preferred. A designer BMP may contain insertions, deletions, and/or substitutions at the N-terminus, C-terminus, or internally. In a preferred embodiment, designed or modified BMPs have at least 1 residue that differs from the most similar human BMP sequence, with at least 2, 3, 4, 5, 6, 7, 8, 9, 10 or more different residues being more preferred.

Designer BMPs of the invention maintain at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity with the corresponding wild-type BMP protein sequence.

Designer BMPs of the invention may maintain at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity with the conserved cysteine domain of the C-terminal region of the corresponding wild-type BMP protein sequence.

Designer BMPs may contain further modifications, for instance mutations that alter additional protein properties such as stability or immunogenicity or which enable or prevent posttranslational modifications such as PEGylation or glycosylation. Designer BMPs may be subjected to co- or post-translational modifications, including but not limited to synthetic derivatization of one or more side chains or termini, glycosylation, PEGylation, circular permutation, cyclization, fusion to proteins or protein domains, and addition of peptide tags or labels.

Due to the degeneracy of the genetic code, an extremely large number of nucleic acids may be made, all of which encode the designer BMPs of the present invention, by simply modifying the sequence of one or more codons in a way that does not change the amino acid sequence of the designer BMP. The designer BMPs of the invention do not comprise these sequences set forth in WO2008/051526 or WO2009/086131.

As described above, BMPs are naturally expressed as pro-proteins comprising a long pro-domain, one or more cleavage sites, and a mature domain. This pro-protein is then processed by the cellular machinery to yield a dimeric mature BMP molecule. In a preferred embodiment, the designer BMPs of the invention are produced in a similar manner. The pro-domain is believed to aid in the correct folding and processing of BMPs. Furthermore, in some but not all BMPs, the pro-domain may noncovalently bind the mature domain and may act as a chaperone, as well as an inhibitor (e.g., Thies et al. (2001) Growth Factors, 18:251-259). Preferably, the modified BMPs of the invention are produced and/or administered therapeutically in this form. Alternatively, BMPs may be produced in other forms, including, but not limited to, where the mature domain is produced directly or refolded from inclusion bodies, or comprises full-length intact pro protein. The designer BMPs of the invention will be useful in these and other forms.

In particular embodiments, the designer BMP of the invention comprises a backbone BMP, i.e., the wild type BMP, to which the designer BMP corresponds. In particular embodiments, this backbone BMP may be a wild type BMP2, BMP4, BMP5, BMP6, BMP7, BMP8, or BMP9 backbone.

In some embodiments of the invention, the designer BMP comprises at least one mutation in a type I binding domain and/or a type II binding domain, wherein the mutation confers altered binding to a type I or type II BMP receptor compared with the binding of a corresponding wild type BMP not comprising the mutation. In some embodiments, the designer BMP comprises at least one mutation in both a type I binding domain and at least one mutation in a type II binding domain. In other embodiments, the designer BMP comprises at least one mutation within the type II binding domain A and the type II binding domain B. In other embodiments, the designer BMP comprises at least one mutation in type II binding domain A, type II binding domain B, and a type I binding domain.

In certain embodiments, the mutation may comprise an amino or nucleic acid substitution, deletion and/or insertion. In a preferred embodiment, the mutation comprises an amino acid substitution.

In some embodiments, the backbone BMP is a wild type BMP and the mutations are one or more of the mutations listed in Tables 4 to 6. The designer BMP may contain any combination and any number of mutations listed in these tables.

In some embodiments, the backbone BMP is a wild type BMP and the mutations are one or more of the mutations listed in Tables 4 to 6. The designer BMP may contain a permutation and any and all of the mutations listed in these tables or disclosed elsewhere herein.

TABLE 4

Type I Binding Domain Mutations

| BMP2 | BMP4 | BMP5 | BMP6 | BMP7 | BMP8 | BMP9 | Possible mutations |
|------|------|------|------|------|------|------|--------------------|
| P48  | P50  | S71  | S72  | A72  | S72  | F42  | F, S, N, A, P      |
| F49  | F51  | F72  | F73  | F73  | F73  | F43  | Y                  |
| A52  | A54  | N75  | N76  | N76  | D76  | A46  | N, A               |
| D53  | D55  | A76  | A77  | S77  | S77  | D47  | A, E, D            |
| H54  | H56  | H77  | H78  | Y78  | C78  | D48  | D, C               |
| L55  | L57  | M78  | M79  | M79  | M79  | V49  | M, V, L            |

TABLE 4-continued

Type I Binding Domain Mutations

| BMP2 | BMP4 | BMP5 | BMP6 | BMP7 | BMP8 | BMP9 | Possible mutations |
|---|---|---|---|---|---|---|---|
| N56 | N58 | N79 | N80 | N80 | N80 | T50 | T, N |
| S57 | S59 | A80 | A81 | A81 | A82 | P51 | A P |
| N59 | N61 | N82 | N83 | N83 | N83 | K53 | K, N |
| V63 | V65 | V86 | V87 | V87 | L87 | V57 | I, V, L |
| T65 | T67 | T88 | T89 | T89 | S89 | T59 | A, T, S |
| N68 | N70 | H91 | H92 | H92 | H92 | H62 | H, N |
| S69 | S71 | L92 | L93 | F93 | L93 | L63 | L, S, F |
| V70 | V72 | M93 | M94 | I94 | M94 | K64 | M, K, I, V |
| N71 | N73 | F94 | N95 | N95 | M95 | F65 | F, N, M |
|  |  | P95 | P96 | P96 | P96 | P66 | INSERT S, P; DELETE P |
| S72 | S74 | D96 | E97 | E97 | D97 | T67 | Q, T, E, D |
| K73 | S75 | H97 | Y98 | T98 | A98 | K68 | Y, H, T, A, K |
| I74 | I76 | V98 | V99 | V99 | V99 | V69 | A, V, I |
| P75 | P77 | P99 | P100 | P100 | P100 | G70 | S, G |

TABLE 5

Type II Binding Domain A Mutations

| BMP2 | BMP4 | BMP5 | BMP6 | BMP7 | BMP8 | BMP9 | Possible mutations |
|---|---|---|---|---|---|---|---|
| V33 | V35 | I56 | I57 | I57 | I57 | I27 | I, V |
| P36 | P38 | E59 | K60 | E60 | Q60 | K30 | K, R, P, E, Q |
| G37 | G39 | G60 | G61 | G61 | G61 | E31 | G, E |
| H39 | Q41 | A62 | A63 | A63 | S63 | E33 | A, E, S, Q |
| F41 | F43 | F64 | N65 | Y65 | Y65 | Y35 | N, Y, F |
| Y42 | Y44 | Y65 | Y66 | Y66 | Y66 | E36 | Y, E |
| H44 | H46 | D67 | D68 | E68 | E68 | K38 | H, D, K, R, E |

TABLE 6

Type II Binding Domain B Mutations

| BMP2 | BMP4 | BMP5 | BMP6 | BMP7 | BMP8 | BMP9 | Possible mutations |
|---|---|---|---|---|---|---|---|
| E83 | E85 | K107 | K108 | Q108 | K108 | K78 | Q, K, E |
| S85 | S87 | N109 | N110 | N110 | S110 | S80 | N, S |
| A86 | A88 | A110 | A111 | A111 | A111 | P81 | P, A |
| M89 | M91 | V113 | V114 | V114 | V114 | V84 | M, V |
| L92 | L94 | F116 | F117 | F117 | Y117 | K87 | F, K, L, Y |
| E94 | E96 | D118 | D119 | D119 | D118 | D89 | D, E |
| N95 | Y97 | S119 | N120 | S120 | S119 | M90 | M, N, S |
| E96 | D98 | S120 | S121 | S121 | S120 | G91 | S, G, D |
| K97 | K99 | N121 | N122 | N122 | N121, N122 | V92 | N, V, K |
| V98 | V100 | V122 | V123 | V123 | V123 | P93 | P, V |
| V99 | V101 | I123 | I124 | I124 | I124 | T94 | T, I, V |

In some embodiments, the mutations improve binding to a type I receptor. In other embodiments improve binding to a type II receptor. In other embodiments, the mutations decrease binding to a type I or type II receptors.

Tables 4-6 above provide a non-limiting compilation of example mutations of the present invention where the position of the mutation is provided relative to the corresponding wild type BMP amino acid sequence. Thus, in some embodiments, the designer BMP comprises the following preferred combinations of mutations:

Exemplary amino acid sequences of designer BMPs are set forth in Table 7, below. Table 7 shows the name and sequence of the designed molecules.

TABLE 7

| NAME | SEQUENCE | SEQ ID NO |
|---|---|---|
| BMP-GE27 | QAKHKQRKRLKSSCKRHPLYVDFSDVGWNDWIIAPEGYAAFYCEGECAFPLNSYMNATNH AIVQTLVHFINPETVPKPCCAPTELNAISVLYFDDSSNVILKNYQDMVVEGCGCR | 8 |

TABLE 7-continued

| NAME | SEQUENCE | SEQ ID NO |
|---|---|---|
| BMP-GE27-NR | QAKHKQRKRLKSSCKRHPLYVDFSDVGWNDWIIAPEGYAAFYCEGECAFPLNSYMNATNH AIVQTLVHFINPETVPKPCCAPTKLRPMSMLYYDDGQNIIKKDIQNMIVEECGCS | 9 |
| BMP-GE46 | SPKHHSQRARKKNKNCRRHSLYVDFSDVGWNDWIIAPKGYAAFYCDGECSFPLNAHMNAT NHAIVQTLVHLMNPEYVPKPCCAPTELNAISVLYFDDNSNVILKNYQEMVVEGCGCR | 10 |
| BMP-GE46-NR | SPKHHSQRARKKNKNCRRHSLYVDFSDVGWNDWIIAPKGYAAFYCDGECSFPLNAHMNAT NHAIVQTLVHLMNPEYVPKPCCAPTKLRPMSMLYYDDGQNIIKKDIQNMIVEECGCS | 11 |
| BMP-GER46 | SPKHHSQRARKKNKNCRRHSLYVDFSDVGWNDWIIAPRGYAAFYCDGECSFPLNAHMNAT NHAIVQTLVHLMNPEYVPKPCCAPTELNAISVLYFDDNSNVILKNYQEMVVEGCGCR | 12 |
| BMP-GER46-NR | SPKHHSQRARKKNKNCRRHSLYVDFSDVGWNDWIIAPRGYAAFYCDGECSFPLNAHMNAT NHAIVQTLVHLMNPEYVPKPCCAPTKLRPMSMLYYDDGQNIIKKDIQNMIVEECGCS | 13 |
| BMP-GE47 | SPKHHSQRARKKNKNCRRHSLYVDFSDVGWNDWIIAPEGYAAFYCEGECAFPLNSYMNAT NHAIVQTLVHFINPETVPKPCCAPTELNAISVLYFDDSSNVILKNYQEMVVEGCGCR | 14 |
| BMP-GE47-NR | SPKHHSQRARKKNKNCRRHSLYVDFSDVGWNDWIIAPEGYAAFYCEGECAFPLNSYMNAT NHAIVQTLVHFINPETVPKPCCAPTKLRPMSMLYYDDGQNIIKKDIQNMIVEECGCS | 15 |

Although the above listed designer BMPs comprise embodiments of the invention, the invention is not limited in any way to any specific molecules. Instead, the invention encompasses any designer BMP comprising altered receptor binding where the designer BMP comprises at least one mutation within a type II receptor binding domain A, even more preferably, the designer BMP comprises at least one further mutation within a type I receptor binding domain, most preferably, the designer BMP comprises yet another at least one further mutation within a type II receptor binding domain B.

In other embodiments, the designer BMP of the present invention comprises an amino acid sequence at least about 70%, 75%, 80%, 85%, 87%, 90%, 92%, 95%, 96%, 97%, 98%, 99% or identical to one of the sequences described above. In another embodiment, the designer BMP comprises an amino acid sequence at least about 70%, 75%, 80%, 85%, 87%, 90%, 92%, 95%, 96%, 97%, 98%, 99% or identical to the sequence of SEQ ID NOs:8-15.

In yet another embodiment, the designer BMP comprises an amino acid sequence as set forth in any one of SEQ ID NOs:8-15. In another embodiment, the amino acid sequence of the designer BMP consists of one of the sequences of SEQ ID NOs:8-15.

Further, in one embodiment, the designer BMP comprises an amino acid sequence at least about 70%, 75%, 80%, 85%, 87%, 90%, 92%, 95%, 96%, 97%, 98%, 99% or identical to one of the sequences of SEQ ID NOS:8-15.

A designer BMP of the invention may comprise a fragment of any one of the sequences described above. In an embodiment, a designer BMP fragment may comprise a fragment of at least an uninterrupted 20, 22, 24, 25, 26, 27, 28, 30, 32, 33, 34, 35, 36, 37, 38, 40, 41, 43, 44, 45, 47, 50, 53, 54, 56, 58, 60, 62, 66, 68, 70, 71, 74, 77, 80, 83, 85, 88, 90, 91, 93, 95, 97, 99, 100, 102, 105, 108, 110, 112, 115, 117, 119, 120, 121, 122, or 125 amino acid sequence from the sequence of any one of the sequences of SEQ ID NOs:8-15.

It is well known in the art that BMPs are often heterogeneous with respect to the amino and/or carboxyl termini of the protein. That is, the present invention comprises a designer BMP comprising an amino acid deletion/truncation at the amino and/or carboxyl terminus comprising a deletion of at least 10 amino acid residues, preferably, 9 amino acid residues, even more preferably, 8 amino acid residues, yet more preferably, 7 amino acid residues, preferably 6 amino acid residues, even more preferably, 5 amino acid residues, preferably 4 amino acid residues, more preferably 3 amino acid residues, even more preferably 2 amino acid residues, and most preferably 1 amino acid reside from the C and or N terminus of the designer BMP.

In another embodiment, the invention comprises a designer BMP protein comprising an amino acid sequence of any one of the sequences of SEQ ID NO:8-15 and further comprising a deletion/truncation from the amino and/or carboxyl termini of the protein. In another embodiment, the invention comprises a designer BMP protein derived from a BMP protein comprising an amino acid sequence of any of the sequences of SEQ ID NOs:8-15, wherein the protein comprises an amino acid deletion/truncation at the amino and/or carboxyl terminus comprising a deletion of at least 10 amino acid residues, preferably, 9 amino acid residues, even more preferably, 8 amino acid residues, yet more preferably, 7 amino acid residues, preferably 6 amino acid residues, even more preferably, 5 amino acid residues, preferably 4 amino acid residues, more preferably 3 amino acid residues, even more preferably 2 amino acid residues, and most preferably 1 amino acid reside from the C and or N terminus of the designer BMP protein amino acid sequence.

Structural Design of BMPs with Altered Receptor Affinity Mediated by Glycosylation The inventors have previously discovered, as explained in Berasi et al. that BMP2 homodimers produced in *E. coli* (referred to herein as "*E. coli* BMP2"), which are not glycosylated, are less active than glycosylated BMP2 produced in mammalian cells, such as CHO cells (referred to herein as "CHO BMP2"). The inventors have also discovered that *E. coli* produced BMP6 homodimers are essentially non-functional compared with BMP6 homodimers produced in mammalian cell culture. These findings indicate that significant variations exist between the crystal structure of *E. coli* BMP2 and CHO BMP2 in the type I receptor binding region.

The inventors have also previously discovered (and disclosed in Berasi et al.) that in mammalian (e.g., CHO) cell produced wild type BMP2, D53 points towards the receptor interface while the H54 points away from the receptor. This is in contrast to *E. coli*-produced BMP2 where the D53 residue points away from the receptor interface and the H54 residue lines up toward the receptor, stacking against a proline reside as illustrated in FIG. 3, apparently acting as a "doorstop." Berasi et al. further demonstrated, for the first time, that CHO-produced BMP6, which is fully glycosylated and active, also comprises a histidine residue pointing toward the incoming receptor, i.e., a histidine "doorstop."

Without wishing to be bound by any particular theory, the inventors' findings, as set forth in Berasi et al. suggested, for the first time, that moving a "doorstop" residue away from the receptor interface can mediate increased binding between the BMP ligand and its receptor. The data further demonstrated that the doorstop residue may be either mutated itself to remove the doorstop or other residues may be mutated to shift the position of the doorstop residue. The data disclosed in Berasi et al. further demonstrated that other residues may be mutated to provide a "glycan tether" which then, in turn, can orient a glycan such that the tethering of the glycan will reorient the doorstop residue.

The present invention, building upon the results in Berasi et al. includes, in some embodiments, a designer BMP produced by incorporating at least one amino acid mutation that affects the glycan tether and/or removes a histidine doorstop structure thereby providing a designer BMP with altered receptor binding.

In summary, in some embodiments, the designer BMPs of the invention may comprise at least one mutation in the type I and/or type II binding domains of BMPs that confer altered type I and/or type II receptor binding. In one embodiment, the BMP sequence is engineered to alter the receptor affinity of BMPs in order to alter and improve the receptor binding and/or osteogenic activity of the engineered or "designer" BMP. In one embodiment, this engineering involves identifying the residues involved in type I and type II receptor binding and replacing them to create designer BMP molecules that show, among other things, higher affinity to both type I and type II receptors than the parental BMP from which the designer is derived.

In other embodiments, the designer BMPs of the invention comprise mutations that create a new arginine "glycan tether" or destroy an existing one to reshape the type I receptor binding domain. That is, the mutation to an arginine in the position two residues C-terminal from the first cysteine, equivalent to R16 of BMP2, appears to cause the glycan chain to be "tethered" onto the BMP surface and consequently alter the conformation of the pre-helical loop region compared with the wild type BMP that lacks the mutation. In other embodiments, the designer BMP of the invention may comprise at least one mutation that alters, creates or destroys (abolishes) the "doorstop" residue that blocks type I receptor from further engagement with BMP. That is, the mutation of H54 in the designer BMP, or a corresponding equivalent residue thereof, that is oriented in such a way that it impedes or increases interaction of the designer BMP with a type I receptor.

In some embodiments, the amino acid mutation affects the conformation of the designer BMP such that the mutation mediates the creation and or abolishment of an arginine "glycan tether" otherwise present in the corresponding wild type BMP. In some embodiments, the mutation mediates an altered conformation which creates or removes/abolishes a histidine doorstop conformation in the designer BMP where such doorstop conformation is either not present or active, respectively, in the corresponding wild type BMP.

Therefore, the skilled artisan, once armed with the teachings provided herein and in Berasi et al., would appreciate that the presence or absence of an arginine "glycan tether" and/or a histidine "doorstop" in a TGFβ superfamily member may be assessed using any method known in the art for the structural analysis of proteins, including, but not limited to, the methods exemplified herein. Once the presence of a "doorstop" residue has been identified, then at least one mutation can be introduced into the molecule to reorient the histidine away from the receptor binding interface. Alternatively, a mutation can be introduced that will create or enhance a "glycan tether" such that the inhibitory effect of the histidine "doorstop", if present, is decreased or, more preferably, eliminated.

In one embodiment, where the TGFβ superfamily member is BMP2, the mutation that removes the histidine doorstop is substitution of another amino acid for H54. In some embodiments, the H54 is replaced with alanine, glycine, serine, or threonine.

Although the present invention discloses such "doorstop"-removing mutations for BMP2, the skilled artisan would understand, based on the knowledge in the art, how to identify corresponding mutations for other TGFβ superfamily members and readily produce mutants lacking a "doorstop," i.e., removing or reorienting a residue that would otherwise interfere with receptor binding by facing or projecting into the binding interface. The effects of the mutation on protein conformation can be determined using any art-recognized method for the structural analysis of proteins such as, but not limited to, those disclosed herein. Alternatively, mutations that can remove the doorstop and increase ligand binding to the type I receptor can be identified in silico using computer modeling methods available in the art. Therefore, the present invention encompasses the design of TGF6 superfamily members having improved binding with the type I receptor in that they lack a histidine "doorstop" residue that would otherwise be present in the receptor interface.

The present invention further provides the skilled artisan with the understanding of how to identify mutations for other TGFβ family members that would generate or destroy the arginine glycan tether. Mutations that add the arginine glycan tether to a protein lacking the tether are contemplated by the instant invention. Therefore, the present invention encompasses the design of TGFβ superfamily members having improved binding with the type I receptor in that they contain an arginine glycan tether that alters the conformation of the type I receptor binding domain.

In some embodiments, the removal of the histidine doorstop thereby removing the requirement of a glycan tether, provides a designer BMP that can be produced without glycosylation while maintaining biological activity. For example, designer BMPs may be produced in cells with glycosylation activity that differs from mammalian cells or is not present, such as bacterial cells, yeast cells, insect cells, or slime mold cells. In particular embodiments, the designer BMPs may be produced in *E. coli* and maintain biological activity.

Thus, in some embodiments, the invention provides methods for designing and producing BMPs that can be produced in cells either lacking glycosylation or comprising altered glycosylation such that an altered glycan is produced which differs from that produced by a mammalian cell. That is, the present invention encompasses methods for introducing a mutation that removes a doorstop residue that would otherwise impair or inhibit receptor binding. The skilled artisan would understand once provided with the teachings of the invention that a doorstop residue that impinges upon the receptor-ligand interface may be mutated to entirely remove the residue or other mutations can be introduced such that the residue is oriented away from the interface. Such other mutations include, but are not limited to, providing a glycan tether that will alter the conformation of a glycan and thereby alter the conformation of the ligand such that the doorstop residue is orientated away from the binding interface.

Nucleic Acids Encoding Designer BMPs

The invention also includes nucleic acids encoding designer the BMPs described herein. Nucleic acids encoding the designer BMPs described herein can be prepared according any one or more suitable means within the wide range of methods known in the art.

In one, nucleic acids encoding designer BMPs are prepared by total gene synthesis, or by site-directed mutagenesis of a nucleic acid encoding wild type or modified BMPs. Methods including template-directed ligation, recursive PCR, cassette mutagenesis, site-directed mutagenesis or other techniques that are well known in the art may be utilized (see for example Strizhov et al., *Proc. Natl. Acad. Sci. USA* 93:15012-15017 (1996); Prodromou and Pen, *Prot. Eng.* 5: 827-829 (1992); Jayaraman and Puccini, *Biotechniques* 12: 392-398 (1992); and Chalmers et al., *Biotechniques* 30: 249-252 (2001)).

Thus, embodiments of the present invention can comprise nucleic acid molecules that encode the designer BMPs of the present invention. In certain embodiments, the invention provides a nucleic acid molecule that encodes for one of the amino acid sequences of SEQ ID NOs:8 to 15.

In other embodiments, the nucleic acid molecule encodes a designer BMP protein that comprises an amino acid sequence at least 70%, 75%, 80%, 85%, 87%, 90%, 92%, 93%, 94%, 95%, 96%, 97%, 98%, 99% identical to one of the amino acid sequences of SEQ ID NOS:8-15.

Methods of Producing Designer BMPs

BMPs are naturally expressed as pro-proteins comprising a long prodomain, one or more cleavage sites, and a mature domain. This pro-protein is then processed by the cellular machinery to yield a, typically, dimeric mature BMP molecule. In some embodiments, the designer BMPs are produced in a similar manner. The prodomain is believed to play a role in the folding and processing of BMPs. Furthermore, in some BMPs, the prodomain may noncovalently bind to the mature protein and act as a solubility enhancer, chaperone, or inhibitor. In some embodiments, BMPs may be produced as mature domains produced directly from or refolded from inclusion bodies. In other embodiments, the BMPs are produced via chemical synthesis or any other known method for protein production.

For instance, in some cases, nucleic acids encoding designer BMPs are prepared by total gene synthesis or by site directed mutagenesis of a nucleic acid encoding a wild type, designer, or variant BMP. Methods include template directed ligation, PCR, cassette mutagenesis, site-directed mutagenesis, restriction enzyme digestion and ligation, or other techniques that are well known in the art (see, e.g., Prodromou et al., Protein Eng 5:827-9 (1992); Jayaraman et al., Biotechniques 12:392-8 (1992); Chalmers et al., Biotechniques 30:249-52 (2001); and Sambrook and Russell, In: Molecular Cloning, A Laboratory Approach, Cold Spring Harbor Press, Cold Spring Harbor, N.Y. (2001)).

In some embodiments, an expression vector that comprises a gene encoding a designer BMP is prepared. Numerous types of appropriate expression vectors and suitable regulatory sequences for a variety of host cells are known in the art. The expression vectors may contain transcriptional and translational regulatory sequences including by not limited to promoter sequences, ribosomal binding sites, transcriptional terminator signals, polyadenylation signals, and enhancer or activator sequences. In some embodiments, the regulatory sequences include a promoter and transcriptional start and stop sequences. In addition, the expression vector may comprise additional elements, such as two replication systems to allow it to be maintained in two organisms. The expression vectors may be extrachromasomal vectors or vectors that integrate into a host cell's genome. In some embodiments, the expression vector contains at least one sequence homologous to a host cell's genome to promote integration into the genome. Constructs for integrating vectors are well known in the art. In some embodiments, the expression vector comprises a selectable marker gene to allow the selection of a stably transformed host cell. Selection marker genes are well known in the art and will vary with the host cell used.

The expression vector may include a secretory leader sequence or signal peptide sequence that provides for secretion of the designer BMP from the host cell. Suitable secretory leader sequences and signal peptides are known in the art.

Nucleic acids encoding designer BMPs may be introduced into host cells either alone or in combination with an expression vector so that the designer BMP is expressed from the nucleic acid. The method of introduction is largely dictated by the host cell type. Exemplary methods of transfection/transformation include $CaPO_4$ precipitation, liposome fusion, electroporation, viral infection, dextran-mediated transfection, polybrene-mediated transfection, protoplast fusion, direct microinjection, and other methods known in the art. Nucleic acids encoding designer BMPs may stable integrate into the host cell genome or may exist transiently or stably in the cytoplasm.

Appropriate host cells for expressing designer BMPs include any cell suitable for expressing wild type or native BMPs, including, but not limited to yeast, bacteria, archaebacteria, fungi, insect, and animal cells. In some embodiments the host cell is *Saccharomyces cerevisiae* or *Escheria coli*. In some embodiments, the host cell is a mammalian cell such as 293 (e.g., 293-T and 293-EBNA), BHK, CHO (e.g., CHOK1 and DG44), COS, Jurkat, NIH3T3, or C2C12 cells. Other suitable cells may be found in the ATCC catalog. Designer BMPs may be produced in more complex organisms, including but not limited to plants and animals. In one embodiment, the cells may be additionally genetically engineered, i.e., to contain exogenous nucleic acids other than the expression vector comprising the designer BMP nucleic acid.

In some embodiments, designer BMPs are produced by culturing a host cell transformed with an expression vector containing a nucleic acid encoding a designer BMP under the appropriate conditions to induce or cause expression of the designer BMP. The conditions appropriate for designer BMP expression are the same conditions known to be appropriate for expressing native or wild type BMPs. These conditions will vary with the choice of expression vector and host cell, and may be easily ascertained by one skilled in the art through routine experimentation.

In some embodiments, the designer BMPs may be purified or isolated after expression. Standard purification methods include electrophoretic, molecular, immunological, and chromatographic techniques, including ion exchange, hydrophobic, affinity, and reverse-phase HPLC chromatography, and chromatofocusing. General guidance in suitable purification techniques may be found in Scopes, In: *Protein Purification*, Springer-Verlag, NY, $3^{rd}$ Ed. (1994). The degree of purification necessary will vary depending on the desired use, and in some instances no purification will be necessary.

Purification from bacterial cells may result in the expression of BMPs in inclusion bodies and a subsequent step of refolding in a CHAPS/High salt system. Purification from mammalian cells may involve a two-step purification via Cellufine-Sulfate and Reversed Phase chromatography columns.

In some embodiments, the designer BMPs may be modified covalently or non-covalently. Covalent modifications may be introduced to a protein by reacting targeted amino acid residues of the protein with an organic derivatizing agent capable of reacting with selected side chains or terminal residues. Optimal sites for modification can be chosen using a variety of criteria, including but not limited to visual inspection, structural analysis, sequence analysis, and molecular simulation.

In some embodiments, designer BMPs may be labeled with at least one element, isotope, or chemical compound. The label may be an isotopic label, such as a radioactive or heavy isotope. In some embodiments, the label may be an immune label such as an antibody or antigen. In some embodiments, the label may be a colored or fluorescent label, such as fluorescein. In some embodiments, the label may be biotin, a tag (e.g., FLAG, Myc, His).

The designer BMPs may be derivatized with bifunctional agents to crosslink a designer BMP to a support matrix or surface for use in purifying antibodies or proteins that bind to the proteins or to detect binding in screening assays. Commonly used crosslinking agents include but are not limited to 1,1-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane. Other modifications include deamidation of glutaminyl and asparaginyl residues to the corresponding glutamyl and aspartyl residues, respectively, hydroxylation of praline and lysine, phosphorylation of hydroxyl groups of seryl or threonyl residues, methylation of the amino groups of lysine, arginine, and histidine side chains (T. E. Creighton, Proteins: Structure and Molecular Properties, W. H. Freeman & Co., San Francisco, pp. 79-86 (1983)), acetylation of the N-terminal amine, and amidation of any C-terminal carboxyl group. Such derivatization may improve the solubility, absorption, transport across the blood brain barrier, serum half-life, and the like. Modifications of designer BMPs may alternatively eliminate or attenuate any possible undesirable side effect of the protein. Moieties capable of mediating such effects are disclosed, for example, in Remington's Pharmaceutical Sciences, 16th ed., Mack Publishing Co., Easton, Pa. (1980).

Another type of covalent modification of designer BMPs comprises linking the protein to one of a variety of nonproteinaceous polymers, e.g., polyethylene glycol ("PEG"), polypropylene glycol, or polyoxyalkylenes, in the manner set forth in U.S. Pat. Nos. 4,640,835; 4,496,689; 4,301,144; 4,670,417; 4,791,192 or 4,179,337. A variety of coupling chemistries may be used to achieve PEG attachment, as is well known in the art.

In another embodiment, the designer BMP comprises linking the protein via a CovX-body linker to a CovX-body antibody such as, but not limited to, the CovX-bodies described in U.S. Pat. No. 5,733,757, and US Patent Publication No. US 2009/0098130. Such CovX-bodies may exhibit improved characteristics, including, but not limited to, improved stability and extended serum half-life.

Methods of Assaying Receptor Binding Activity of Designer BMPs

The receptor binding activity of designer BMPs may be assessed using any methods used for assessing the activity of wild type BMPs.

The affinity of designer BMPs for one or more BMP receptors can be determined by receptor binding assays. For example, affinities for ALK-2, ALK-3, ALK-6, ActRII, ActRIIb, or BMPRII can be determined. Suitable binding assays include, but are not limited to ELISA, fluorescence anisotropy and intensity, scintillation proximity assays (SPA), Biacore (Pearce et al., *Biochemistry* 38:81-89 (1999)), DELFIA assays, and AlphaScreen™ (commercially available from PerkinElmer; Bosse R., Illy C, and Chelsky D (2002)).

In some embodiments, Biacore or surface plasmon resonance assays are used. See, for example, McDonnell, *Curr. Opin. Chem. Biol.* 5:572-577 (2001). Biacore experiments have been used previously to characterize binding of TGF-β isoforms to their receptors (De Crescenzo et al., J. Biol. Chem., 276: 29632-29643 (2001); De Crescenzo et al., J. Mol. Biol. 328: 1173-1183) (2003).

In other embodiments, a plate-based Direct Binding Assay is used to determine the affinity of one or more modified BMPs for one or more BMP receptors. This method is a modified sandwich ELISA in which BMP is captured using an anti-BMP monoclonal antibody and then detected using a BMP receptor-Fc fusion protein.

In other embodiments, AlphaScreen™ assays (Bosse R. et al., Principles of AlphaScreen™, PerkinElmer Literature Application Note Ref #4069, (2002)) can be used to characterize receptor and inhibitor binding. Fluorescence assays may also be used to characterize receptor and inhibitor binding. For example, either BMP2 or a BMP2 receptor or inhibitor may be labeled with a fluorescent dye (for examples of suitable dyes, see the Molecular Probes catalog). Additionally, scintillation proximity assays (SPA) can be used to determine receptor binding affinity. For example, BMP receptor-Fc fusions may be bound to protein A coated SPA beads or flash-plate and treated with S35-labeled BMP; the binding event results in production of light.

In a particular embodiment, the KD of a specific BMP mutant to a Type I or Type II receptor can be determined by using receptor extracellular domain fusions to a human IgG-Fc. The receptor can be bound to an octet sensor using anti-human-IgG-Fc sensors and the BMP can bind the receptor extra-cellular domain in solution to determine Kon and Koff rates. The Octet systems utilize proprietary Bio-Layer Interferometry (BLI) to enable real-time, label-free analysis of biomolecular interactions and to provide information on affinity, kinetics and concentration. As proteins bind the Octet sensor the light passing through the sensor has a wavelength shift that can be measured with a spectrophotometer. The rate of the shift is measured as the analyte binds the sensor and when it loses binding.

Methods of Assaying Osteogenic Activity of Designer BMP

The osteogenic activity of designer BMPs may be assessed using any methods used for assessing the activity of wild type BMPs.

BMPs promote the growth and differentiation of a number of types of cells. Differentiation may be monitored using, for example, luminescence reporters for alkaline phosphatase or calorimetric reagents such as Alcian Blue or PNPP (Asahina et al. (1996) Exp. Cell Res, 222:38-47; inada et al. (1996) Biochem. Biophys. Res. Commun. 222:317-322; Jortikka et al. (1998) Life ScL 62:2350-2368; Cheng et al. (2003) J. Bone Joint Surgery 95A:1544-1552).

The rat limb bud cartilage differentiation assay may also be used to monitor activity in primary cells. In alternative embodiments, reporter gene or kinase assays may be used. Since BMPs activate the JAK-STAT signal transduction pathway, a BMP responsive cell line containing a STAT-responsive reporter such as GFP or luciferase may be used (Kusanagi et al. (2000) Mol Cell., 11:555-565). For example, BMP activity in kidney cells may be determined using cell-based assays; see for example Wang and Hirschberg (2004) J. Biol. Chem., 279:23200-23206.

Osteogenic activity may be measured in cell based assays such as alkaline phosphatase, BRE luciferase, or Alizarin red mineralization, all of which are described in Isaacs et al., *Mol. Endocrinol.* 24:1469-41477 (2010).

Osteogenic activity may also be measured in vivo, via rat ectopic bone assays or mammalian bone growth models. In some embodiments, osteogenic activity is measured in non-human primate models. These models are described in Isaacs et al., *Mol. Endocrinol.* 24:14691477 (2010).

Methods for evaluating bone mass and quality are known in the art and include, but are not limited to X-ray diffraction; DXA DEOCT; pOCT, chemical analysis, density fractionation, histophotometry, histomorphometry, and histochemical analysis as described, for example, in Lane et al., *J. Bone Min. Res.* 18:2105-2115 (2003). One assay for determining cortical bone density is the MicroCT assay. Following pQCT measurement, the microCT evaluation can be performed, for example, using a Scanco mCT40 (Scanco Medical AG) on a femur.

Any known or later developed in vitro or in vivo method for assessing bone growth/density/strength may be used to assess the osteogenic activity of the designer BMPs of the invention.

Pharmaceutical Compositions

Designer BMPs of the present invention may be formulated for administration to a mammal, preferably a human in need thereof as part of a pharmaceutical composition. The composition can be administered by any suitable means, e.g., parenterally, orally or locally. Where the designed BMPs is to be administered locally, as by injection, to a desired tissue site, or systemically, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or aerosol administration, the composition preferably comprises an aqueous solution. The solution preferably is physiologically acceptable, such that administration thereof to a mammal does not adversely affect the mammal's normal electrolyte and fluid volume balance. The aqueous solution thus can comprise, e.g., normal physiologic saline (0.9% NaCl, 0.15M), pH 7-7.4.

Useful solutions for oral or parenteral systemic administration can be prepared by any of the methods well known in the pharmaceutical arts, described, for example, in "Remington's Pharmaceutical Sciences" (Gennaro, A., ed., Mack Pub., 1990, the disclosure of which is incorporated herein by reference). Formulations can include, for example, polyalkylene glycols such as polyethylene glycol, oils of vegetable origin, hydrogenated naphthalenes, and the like. Formulations for direct administration, in particular, can include glycerol and other compositions of high viscosity.

Biocompatible, preferably bioresorbable polymers, including, for example, hyaluronic acid, collagen, tricalcium phosphate, polybutyrate, polylactide, polyglycolide and lactide/glycolide copolymers, may be useful excipients to control the release of the designer BMPs in vivo. Other potentially useful parenteral delivery systems for the present designer BMPs can include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate or deoxycholate, or oily solutions for administration in the form of nasal drops or as a gel to be applied intranasally.

Alternatively, the designer BMPs of the invention may be administered orally. For example, liquid formulations of designer BMPs can be prepared according to standard practices such as those described in "Remington's Pharmaceutical Sciences" (supra). Such liquid formulations can then be added to a beverage or another food supplement for administration. Oral administration can also be achieved using aerosols of these liquid formulations. Alternatively, solid formulations prepared using art-recognized emulsifiers can be fabricated into tablets, capsules or lozenges suitable for oral administration.

Optionally, the designer BMPs can be formulated in compositions comprising means for enhancing uptake of the protein by a desired tissue. For example, tetracycline and diphosphonates (bisphosphonates) are known to bind to bone mineral, particularly at zones of bone remodeling, when they are provided systemically in a mammal. Accordingly, such components can be used to enhance delivery of the present designer BMPs to bone tissue. Alternatively, an antibody or portion thereof that binds specifically to an accessible substance specifically associated with the desired target tissue, such as a cell surface antigen, also can be used. If desired, such specific targeting molecules can be covalently bound to the present designer BMP, e.g. by chemical crosslinking or by using standard genetic engineering techniques to create, for example, an acid labile bond such as an Asp-Pro linkage. Useful targeting molecules can be designed, for example, according to the teachings of U.S. Pat. No. 5,091,513.

It is contemplated also that some of the designer BMPs may exhibit the highest levels of activity in vivo when combined with carrier matrices, including without limitation polymer matrices. See for example, U.S. Pat. No. 5,266,683 the disclosure of which is incorporated by reference herein. Currently preferred carrier matrices are xenogenic, allogenic or autogenic in nature. It is contemplated, however, that synthetic materials comprising polylactic acid, polyglycolic acid, polybutyric acid, derivatives and copolymers thereof may also be used to generate suitable carrier matrices. Preferred synthetic and naturally derived matrix materials, their preparation, methods for formulating them with the designer BMPs of the invention, and methods of administration are well known in the art and so are not discussed in detailed herein. See for example, U.S. Pat. No. 5,266,683.

In certain embodiments, the designer BMPs can be administered to the mammal in need thereof either alone or in combination with another substance known to have a beneficial effect on tissue morphogenesis. Examples of such substances (herein, cofactors) include substances that promote tissue repair and regeneration and/or inhibit inflammation or fibrosis. Examples of useful cofactors for stimulating bone tissue growth in osteoporotic individuals, for example, include but are not limited to, vitamin D3, calcitonin, prostaglandins, parathyroid hormone, dexamethasone, estrogen and IGF-I or IGF-II. Useful cofactors for nerve tissue repair and regeneration can include nerve growth factors. Other useful cofactors include symptomalleviating cofactors, including antiseptics, antibiotics, antiviral and antifungal agents, analgesics and anesthetics.

Designer BMPs are preferably formulated into pharmaceutical compositions by admixture with pharmaceutically acceptable, nontoxic excipients and carriers. As noted above, such compositions can be prepared for systemic, e.g., parenteral, administration, particularly in the form of liquid solutions or suspensions; for oral administration, particularly in the form of tablets or capsules; or intranasally, particularly in the form of powders, nasal drops or aerosols. Where adhesion to a tissue surface is desired, the composition can comprise a fibrinogen-thrombin dispersant or other bioadhesive such as is disclosed, for example, in PCT US91/09275, the disclosure of which is incorporated herein by reference. The composition then can be painted, sprayed or otherwise applied to the desired tissue surface.

When administered, the pharmaceutical composition of this invention is typically delivered in a pyrogen-free, physiologically acceptable form. Further, the composition may desirably be encapsulated or injected in a viscous form for delivery to the site of bone cartilage or tissue damage. Local administration may be suitable for wound healing and tissue repair. Preferably for bone and/or cartilage formation, the composition includes a matrix capable of delivering BMP protein to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the designer BMP compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above-mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the designer BMP protein. These factors include, without limitation, the amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution. The addition of other known growth factors, such as IGF I (insulin like growth factor I), to the final composition, may also effect the dosage. Progress can be monitored by periodic assessment of bone growth and/or repair. One method of assessing bone growth or repair is by x-ray imaging and/or CT scanning, among many art-recognized methods.

The compositions can be formulated for parenteral or oral administration to humans or other mammals in therapeutically effective amounts, e.g., amounts which provide appropriate concentrations of the designer BMPs to target tissue for a time sufficient to induce the desired effect. Preferably, the present compositions alleviate or mitigate the mammal's need for a morphogen-associated biological response, such as maintenance of tissue-specific function or restoration of tissue-specific phenotype to senescent tissues (e.g., osteopenic bone tissue) or the inhibition or reversal of a fibrotic response in a tissue.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. The preferred dosage of drug to be administered also is likely to depend on such variables as the type and extent of a disease, tissue loss or defect, the overall health status of the particular patient, the relative biological efficacy of the compound selected, the formulation of the compound, the presence and types of excipients in the formulation, and the route of administration.

In general terms, the compounds of this invention may be provided in an aqueous physiological buffer solution containing about 0.1 to 10% w/v compound for parenteral administration. Typical doses ranges are from about 10 ng/kg to about 1 g/kg of body weight per day; with a preferred dose range being from about 0.1 mg/kg to 100 mg/kg of body weight.

Therapeutic Uses

Designer BMPs may be used for any indication that wild type BMPs are useful for or for any method in which a TGFβ superfamily member can be used. Designer BMPs are capable of inducing the developmental cascade of bone and cartilage morphogenesis and to induce or mediate Smad signaling pathways. Designer BMPs induce greater bone augmentation and repair, including, but not limited to, production of greater bone mass, bone stiffness and bone density that corresponding wild type BMP. Accordingly, designer BMPs may be used to induce bone formation in a tissue. Also, designer BMPs may be used to induce proliferation of bone and cartilage in a variety of locations in the body. For example, designer BMPs may be used to repair joints such as knee, elbow, ankle, and finger. For example, designer BMPs may be useful for regenerating cartilage in patients suffering from arthritis or other cartilage degenerating diseases. Further, designer BMPs are indicated for treating tears in cartilage due to injury. In addition, designer BMPs are useful for inducing bone growth in patients. For example, designer BMPs are indicated for use in treating patients suffering from bone fractures or breaks, osteoporosis, or patients in need of spinal fusion or for repair of the spine, vertebrae or the like.

In another embodiment, the invention includes a method of bone augmentation and/or repair. Thus, the invention encompasses administering a therapeutically effective amount of a designer BMP to a site where it mediates detectable bone augmentation or repair.

In another embodiment, the invention includes a method of inducing or increasing Smad expression. The method comprises contacting a cell comprising Smad mediated expression pathway with a designer BMP of the invention.

Designer BMPs are capable of inducing the developmental cascade of bone morphogenesis and tissue morphogenesis for a variety of tissues in mammals different from bone or bone cartilage. This morphogenic activity includes the ability to induce proliferation and differentiation of progenitor cells, and the ability to support and maintain the differentiated phenotype through the progression of events that results in the formation of bone, cartilage, non-mineralized skeletal or connective tissues, and other adult tissues.

For example, designer BMPs may be used for treatment to prevent loss of and/or increase bone mass in metabolic bone diseases. General methods for treatment to prevent loss of and/or increase bone mass in metabolic bone diseases using osteogenic proteins are disclosed in U.S. Pat. No. 5,674,844, the disclosures of which are hereby incorporated by reference. Designer BMPs may also be administered to replace or repair bone or cartilage at injury sites such as bone breaks, bone fractures, and cartilage tears.

Designer BMPs of the present invention may be used for periodontal tissue regeneration. General methods for periodontal tissue regeneration using osteogenic proteins are disclosed in U.S. Pat. No. 5,733,878, the disclosures of which are hereby incorporated by reference.

Designer BMPs may be used for liver regeneration. General methods for liver regeneration using osteogenic proteins are disclosed in U.S. Pat. No. 5,849,686, the disclosures of which are hereby incorporated by reference. Designer BMPs may be used for treatment of chronic renal failure. General methods for treatment of chronic renal failure using osteogenic proteins are disclosed in U.S. Pat. No. 6,861,404, the disclosures of which are hereby incorporated by reference. Designer BMPs may be used for enhancing functional recovery following central nervous system ischemia or trauma. General methods for enhancing functional recovery following central nervous system ischemia or trauma using osteogenic proteins are disclosed in U.S. Pat. No. 6,407,060, the disclosures of which are hereby incorporated by reference.

Designer BMPs may be used for inducing dendritic growth. General methods for inducing dendritic growth using osteogenic proteins are disclosed in U.S. Pat. No. 6,949,505, the disclosures of which are hereby incorporated by reference.

Designer BMPs may be used for inducing neural cell adhesion. General methods for inducing neural cell adhesion using osteogenic proteins are disclosed in U.S. Pat. No. 6,800,603, the disclosures of which are hereby incorporated by reference.

Designer BMPs may be used for treatment and prevention of Parkinson's disease. General methods for treatment and prevention of Parkinson's disease using osteogenic proteins are disclosed in U.S. Pat. No. 6,506,729, the disclosures of which are hereby incorporated by reference.

It is within skills of an ordinary artisan to modify the general methods using the modified BMPs of the present invention for various therapeutic uses described above. Exemplary embodiments of therapeutic applications of the modified BMPs of the present invention are further described below.

Designer BMPs may be used to repair diseased or damaged mammalian tissue. The tissue to be repaired is preferably assessed, and excess necrotic or interfering scar tissue removed as needed, by surgical, chemical, ablating or other methods known in the medical arts. The designer BMPs then may be provided directly to the tissue locus as part of a sterile, biocompatible composition, either by surgical implantation or injection. Alternatively, a sterile, biocompatible composition containing modified BMP-stimulated progenitor cells may be provided to the tissue locus. The existing tissue at the locus, whether diseased or damaged, provides the appropriate matrix to allow the proliferation and tissue-specific differentiation of progenitor cells. In addition, a damaged or diseased tissue locus, particularly one that has been further assaulted by surgical means, provides a morphogenically permissive environment. For some tissues, it is envisioned that systemic provision of the modified BMPs will be sufficient.

Designer BMPs may be used to prevent or substantially inhibit scar tissue formation following an injury. If a designer BMP is provided to a newly injured tissue locus, it can induce tissue morphogenesis at the locus, preventing the aggregation of migrating fibroblasts into non-differentiated connective tissue. The designer BMP preferably is provided as a sterile pharmaceutical preparation injected into the tissue locus within five hours of the injury.

For example, the designer BMPs may be used for protein-induced morphogenesis of substantially injured liver tissue following a partial hepatectomy. Variations on this general protocol may be used for other tissues. The general method involves excising an essentially nonregenerating portion of a tissue and providing the modified BMP, preferably as a soluble pharmaceutical preparation to the excised tissue locus, closing the wound and examining the site at a future date. Like bone, liver has a potential to regenerate upon injury during post-fetal life.

As another example, designer BMPs can also be used to induce dentinogenesis. To date, the unpredictable response of dental pulp tissue to injury is a basic clinical problem in dentistry. Using standard dental surgical procedures, small areas (e.g., 2 mm) of dental pulps can be surgically exposed by removing the enamel and dentin immediately above the pulp (by drilling) of sample teeth, performing a partial amputation of the coronal pulp tissue, inducing hemostasis, application of the pulp treatment, and sealing and filling the cavity by standard procedures.

The designer BMPs of the invention may be used to treat fibrosis. The fibrosis may be located in various parts of the body and can be of a particular kind, for example, the fibrosis may be located: in the kidney, for example, fibrosis as observed in glomerulonenephritis, diabetic nephropathy, allograft rejection, and HIV nephropathy; in the liver, for example, cirrhosis, and veno-occlusive disease; in the lung, for example, idiopathic fibrosis (and autoimmune fibrosis); in the skin, for example, systemic sclerosis, keloids, scars, and eosinophilia-myalgia syndrome; in the central nervous system, for example, intraocular fibrosis; in the cardiovascular system, for example, vascular restenosis; in the nose, for example, nasal polyposis; in bone or bone marrow; in an endocrine organ; and in the gastrointestinal system.

In one embodiment, a designer BMP having the binding characteristics of BMP7, or useful modification thereof (extended half life, increase binding affinity for a same or different receptor compared with wild type BMP7, resistance to inhibition by a BMP7 antagonist, such as, but not limited to, Noggin, and the like) may be useful to treat, ameliorate or reverse fibrosis. That is, as reviewed recently in Weiskirchen et al., 2009, Frontiers in Biosci. 14:4992-5012, TGFβ$_1$ mediates a cascade leading to increased fibrosis, including, but not limited to, epithelial-to-mesenchymal transition. The fibrosis-inducing effects of TGFβ$_1$ may be inhibited or reversed by BMP7. See also Loureiro et al., 2010, Nephrol. Dial. Transplant. 25:1098-1108. Further, certain fribotic conditions may also be treated or ameliorated by administration of BMP4 (see Pegorier et al., 2010, Resp. Res. 11:85). Therefore, the invention encompasses a designer BMP either based on a BMP7 framework and/or incorporating the type I and type II mutations disclosed elsewhere herein, to alter receptor binding and provide a potential useful therapeutic for treatment of fibrosis in a patient in need thereof.

A fibrotic disorder may be induced by a number of causes including: chemotherapy, for example, pulmonary fibrosis resulting from bleomycin, chlorambucil, cyclophsphamide, methotrexate, mustine, or procarbazine treatment; radiation exposure whether accidental or purposeful as in radiation therapy, for example, interstitial lung disease (ILD) resulting from radiation; environmental or industrial factors or pollutants such as chemicals, fumes, metals, vapors, gases, etc., for example, ILD resulting from asbestos or coal dust; a drug or a combination of drugs, for example, antibiotics (e.g. penicillins, sulfonamides, etc.), cardiovascular drugs (e.g., hydralazine, beta blockers, etc.), CNS drugs (phenytoin, chlorpromazine, etc.) anti-inflammatory drugs (e.g., gold salts, phenylbutazone, etc.), etc. can cause ILD; an immune reaction disorder, for example, chronic graft-versus-host disease with dermal fibrosis; disease states such as aspiration pneumonia which is a known cause of ILD, and parasite induced fibrosis; and wounds, for example, blunt trauma, surgical incisions, battlefield wounds, etc., as in penetrating injuries of the CNS.

In a particular embodiment, designer BMPs with improved binding to type I receptor ALK2, such as BMPE, may be used to treat diseases related to ALK2.

Kits

The invention includes various kits which comprise a therapeutically effective amount of a designer BMP of the invention, along with an applicator and instructional materials which describe use of the designer BMP to perform the methods of the invention. Although exemplary kits are described below, the contents of other useful kits will be apparent to the skilled artisan in light of the present disclosure. Each of these kits is included within the invention.

The invention includes a kit for treatment to prevent loss of and/or increase bone mass in a metabolic bone disease in a patient in need thereof. The kit includes a designer BMP of the invention. The kit further comprises an applicator, including, but not limited to, a syringe, a bone cement mixing device, and the like, for administration of the components of the kit to a patient. Further, the kit comprises an instructional material setting forth the pertinent information for the use of the kit to treat or prevent bone mass and/or increase bone mass in the patient.

More preferably, the kit comprises at least one designer BMP selected from an antibody having an amino acid sequence selected from the amino acid sequence of SEQ ID NOs:8-15, i.e. the designer BMP comprises the amino acid sequence of SEQ ID NO:8, SEQ ID NO:9, SEQ ID NO:10 and SEQ ID NO:11, SEQ ID NO:12, SEQ ID NO:13, SEQ ID NO:14 and/or SEQ ID NO:15.

The kit can comprise any number of additional therapeutic agents for treatment to prevent bone loss and/or increase bone mass. Such agents are set forth previously and include therapeutic compounds, cytokines, vitamins, other members of the TGFβ superfamily, among many others.

The invention also relates to an article of manufacture (e.g., dosage form adapted for i.v. or oral administration) comprising a designer BMP in the amount effective to prevent bone loss and/or increase bone mass (e.g., more than 10 mg/kg, at least 15 mg/kg, or 15 mg/kg). In certain embodiments, the article of manufacture comprises a container or containers comprising a designer BMP and a label and/or instructions for use to treat or prevent bone loss and/or increase bone mass.

The invention also includes a kit to treat or prevent fibrosis in a tissue or organ in a patient in need thereof. The kit includes a designer BMP of the invention. The kit further comprises an applicator, including, but not limited to, a syringe or device for delivering the protein, a mixing device, and the like, for administration of the components of the kit to a patient. Further, the kit comprises an instructional material setting forth the pertinent information for the use of the kit to treat or prevent fibrosis in the patient.

More preferably, the kit comprises at least one designer BMP selected from a protein having an amino acid sequence selected from the amino acid sequence of SEQ ID NOs:8-15, i.e. the designer BMP comprises the amino acid sequence of SEQ ID NO:8, SEQ ID NO:9, SEQ ID NO:10 and SEQ ID NO:11, SEQ ID NO:12, SEQ ID NO:13, SEQ ID NO:14 and/or SEQ ID NO:15.

The kit can comprise any number of additional therapeutic agents for treatment to prevent bone loss and/or increase bone mass or treat or prevent fibrosis. Such agents are set forth previously and include therapeutic compounds, cytokines, vitamins, other members of the TGFβ superfamily, among many others.

The invention also relates to an article of manufacture (e.g., dosage form adapted for i.v. or oral administration) comprising a designer BMP in the amount effective to prevent bone loss and/or increase bone mass or to treat or prevent fibrosis (e.g., more than 1 mg/kg, at least 10 mg/kg, at least 15 mg/kg, or 15 mg/kg). In certain embodiments, the article of manufacture comprises a container or containers comprising a designer BMP and a label and/or instructions for use to treat or prevent bone loss and/or increase bone mass or to treat or prevent fibrosis.

Listing of Exemplary Embodiments

The following non-limiting embodiments are illustrative of various embodiments of the present invention:

1. A designer BMP protein comprising the amino acid sequence of any one of SEQ ID NOs: 8, 9, 10, 11, 12, 13, 14 or 15.
2. The designer BMP protein of embodiment 1, further comprising at least one mutation, the mutation not being within a Type I, Type IIA, or Type IIB binding domain of the designer BMP protein.
3. The designer BMP protein of embodiment 2, wherein the at least one mutation is not more than 10 mutations.
4. The designer BMP protein of embodiment 1, having a binding profile which differs from a binding profile of a corresponding wild-type BMP.
5. The designer BMP protein of embodiment 4, wherein the binding profile of the designer BMP protein includes at least one of the following: binding to the ALK2 receptor with a $K_D$ not greater than about 2 nM; binding to the ALK3 receptor with a $K_D$ not greater than about 2 nM; binding to the ALK6 receptor with a $K_D$ not greater than about 1 nM; binding to the ActRIIA receptor with a $K_D$ not greater than about 2 nM; binding to the ActRIIB receptor with a $K_D$ not greater than about 0.5 nM; and binding to the BMPRIIA receptor with a $K_D$ not greater than about 3.5 nM.
6. A nucleic acid encoding the designer BMP protein of embodiment 1.
7. A method of producing a designer BMP protein comprising the steps of introducing an expression vector comprising the nucleic acid of embodiment 6 into a cell.
8. A method of treating a patient, comprising the step of contacting the patient with a designer BMP protein according to embodiment 1.
9. The method of embodiment 8, wherein treating a patient comprises treating a bone disease associated with bone loss, and wherein the step of contacting a patient with a designer BMP includes administering to the patient a dose of the designer BMP effective to treat the bone disease.

10. The method of embodiment 8, wherein treating a patient comprises treating fibrosis, and wherein the step of contacting a patient with a designer BMP includes administering to the patient a dose of the designer BMP effective to treat fibrosis.

11. A designer BMP protein comprising the following mutations relative to SEQ ID NO:1: V33I, P36E, H39A, H44E, P48A, A52N, D53S, H54Y, L55M, S57A, N68H, S69F, V70I, S72P, K73E, insertion of a T following K73, I74V, A77P, V80A, S85N, M89V, L92F, E94D, N95S, E96S, K97N, V99I.

12. The designer BMP protein of embodiment 11, further comprising at least one mutation, the mutation not being within a Type I, Type IIA, or Type IIB binding domain of the designer BMP protein.

13. The designer BMP protein of embodiment 11, comprising the amino acid sequence of SEQ ID NO: 8.

14. The designer BMP protein of embodiment 11, having a binding profile which differs from a binding profile of a corresponding wild-type BMP.

15. The designer BMP protein of embodiment 14, wherein the binding profile of the designer BMP protein includes at least one of the following: binding to the ALK2 receptor with a $K_D$ not greater than about 2 nM; binding to the ALK3 receptor with a $K_D$ not greater than about 2 nM; binding to the ALK6 receptor with a $K_D$ not greater than about 1 nM; binding to the ActRIIA receptor with a $K_D$ not greater than about 2 nM; binding to the ActRIIB receptor with a $K_D$ not greater than about 0.5 nM; and binding to the BMPRIIA receptor with a $K_D$ not greater than about 3.5 nM.

16. A nucleic acid encoding the designer BMP protein of embodiment 11.

17. A method of producing a designer BMP protein comprising the steps of introducing an expression vector comprising the nucleic acid of embodiment 16 into a cell.

18. A method of treating a patient, comprising the step of contacting the patient with a designer BMP protein according to embodiment 11.

19. The method of embodiment 18, wherein treating a patient comprises treating a bone disease associated with bone loss, and wherein the step of contacting a patient with a designer BMP includes administering to the patient a dose of the designer BMP effective to treat the bone disease.

20. The method of embodiment 18, wherein treating a patient comprises treating fibrosis, and wherein the step of contacting a patient with a designer BMP includes administering to the patient a dose of the designer BMP effective to treat fibrosis.

21. A designer BMP protein comprising the following mutations relative to SEQ ID NO:1: V33I, P36E, H39A, H44E, P48A, A52N, D53S, H54Y, L55M, S57A, N68H, S69F, V70I, S72P, K73E, insertion of a T following K73, I74V, A77P, V80A, E83K, S85R, A86P, I87M, L92Y, E94D, N95G, E96Q, K97N, V98I, V99I, L100K, N102D, Y103I, D105N, V107I, G110E, R114S.

22. The designer BMP protein of embodiment 21, further comprising at least one mutation, the mutation not being within a Type 1, Type IIA, or Type IIB binding domain of the designer BMP protein.

23. The designer BMP protein of embodiment 21, comprising the amino acid sequence of SEQ ID NO: 9.

24. The designer BMP protein of embodiment 21, having a binding profile which differs from a binding profile of a corresponding wild-type BMP.

25. The designer BMP protein of embodiment 24, wherein the binding profile of the designer BMP protein includes at least one of the following: binding to the ALK2 receptor with a $K_D$ not greater than about 2 nM; binding to the ALK3 receptor with a $K_D$ not greater than about 2 nM; binding to the ALK6 receptor with a $K_D$ not greater than about 1 nM; binding to the ActRIIA receptor with a $K_D$ not greater than about 2 nM; binding to the ActRIIB receptor with a $K_D$ not greater than about 0.5 nM; and binding to the BMPRIIA receptor with a $K_D$ not greater than about 3.5 nM.

26. A nucleic acid encoding the designer BMP protein of embodiment 21.

27. A method of producing a designer BMP protein comprising the steps of introducing an expression vector comprising the nucleic acid of embodiment 26 into a cell.

28. A method of treating a patient, comprising the step of contacting the patient with a designer BMP protein according to embodiment 21.

29. The method of embodiment 28, wherein treating a patient comprises treating a bone disease associated with bone loss, and wherein the step of contacting a patient with a designer BMP includes administering to the patient a dose of the designer BMP effective to treat the bone disease.

30. The method of embodiment 28, wherein treating a patient comprises treating fibrosis, and wherein the step of contacting a patient with a designer BMP includes administering to the patient a dose of the designer BMP effective to treat fibrosis.

31. A designer BMP protein comprising the following mutations relative to SEQ ID NO:2: V35I, P38K, Q41A, H46D, D48E, P50S, A54N, D55A, L57M, S59A, N70H, S71L, V72P, S74P, S75E, insertion of a Y after S75, I76V, A79P, V82A, S87N, M91V, L94F, E96D, Y97N, D98S, K99N, V101I.

32. The designer BMP protein of embodiment 31, further comprising at least one mutation, the mutation not being within a Type I, Type IIA, or Type IIB binding domain of the designer BMP protein.

33. The designer BMP protein of embodiment 31, comprising the amino acid sequence of one of SEQ ID NOS: 10 or 12.

34. The designer BMP protein of embodiment 31, having a binding profile which differs from a binding profile of a corresponding wild-type BMP.

35. The designer BMP protein of embodiment 34, wherein the binding profile of the designer BMP protein includes at least one of the following: binding to the ALK2 receptor with a $K_D$ not greater than about 2 nM; binding to the ALK3 receptor with a $K_D$ not greater than about 2 nM; binding to the ALK6 receptor with a $K_D$ not greater than about 1 nM; binding to the ActRIIA receptor with a $K_D$ not greater than about 2 nM; binding to the ActRIIB receptor with a $K_D$ not greater than about 0.5 nM; and binding to the BMPRIIA receptor with a $K_D$ not greater than about 3.5 nM.

36. A nucleic acid encoding the designer BMP protein of embodiment 31.

37. A method of producing a designer BMP protein comprising the steps of introducing an expression vector comprising the nucleic acid of embodiment 36 into a cell.

38. A method of treating a patient, comprising the step of contacting the patient with a designer BMP protein according to embodiment 31.

39. The method of embodiment 38, wherein treating a patient comprises treating a bone disease associated with bone loss, and wherein the step of contacting a patient with a designer BMP includes administering to the patient a dose of the designer BMP effective to treat the bone disease.

40. The method of embodiment 38, wherein treating a patient comprises treating fibrosis, and wherein the step of contacting a patient with a designer BMP includes administering to the patient a dose of the designer BMP effective to treat fibrosis.

41. A designer BMP protein comprising the following mutations relative to SEQ ID NO:2: V35I, P38K, Q41A, H46D, D48E, P50S, A54N, D55A, L57M, S59A, N70H, S71L, V71M, S74P, S75E, insertion of a Y after S75, I76V, A79P, V82A, E85K, S87R, A88P, I89M, L94Y, E96D, Y97G, D98Q, K99N, V100I, V101OI, L102K, N104D, Y105I, E107N, V109I, G112E, R116S.

42. The designer BMP protein of embodiment 41, further comprising at least one mutation, the mutation not being within a Type 1, Type IIA, or Type IIB binding domain of the designer BMP protein.

43. The designer BMP protein of embodiment 41, comprising the amino acid sequence of SEQ ID NO: 11.

44. The designer BMP protein of embodiment 41, having a binding profile which differs from a binding profile of a corresponding wild-type BMP.

45. The designer BMP protein of embodiment 44, wherein the binding profile of the designer BMP protein includes at least one of the following: binding to the ALK2 receptor with a $K_D$ not greater than about 2 nM; binding to the ALK3 receptor with a $K_D$ not greater than about 2 nM; binding to the ALK6 receptor with a $K_D$ not greater than about 1 nM; binding to the ActRIIA receptor with a $K_D$ not greater than about 2 nM; binding to the ActRIIB receptor with a $K_D$ not greater than about 0.5 nM; and binding to the BMPRIIA receptor with a $K_D$ not greater than about 3.5 nM.

46. A nucleic acid encoding the designer BMP protein of embodiment 41.

47. A method of producing a designer BMP protein comprising the steps of introducing an expression vector comprising the nucleic acid of embodiment 46 into a cell.

48. A method of treating a patient, comprising the step of contacting the patient with a designer BMP protein according to embodiment 41.

49. The method of embodiment 48, wherein treating a patient comprises treating a bone disease associated with bone loss, and wherein the step of contacting a patient with a designer BMP includes administering to the patient a dose of the designer BMP effective to treat the bone disease.

50. The method of embodiment 48, wherein treating a patient comprises treating fibrosis, and wherein the step of contacting a patient with a designer BMP includes administering to the patient a dose of the designer BMP effective to treat fibrosis.

51. A designer BMP protein comprising the following mutations relative to SEQ ID NO:2: V35I, P38R, Q41A, H46D, D48E, P50S, A54N, D55A, L57M, S59A, N70H, S71L, V72M, S74P, S75E, insertion of a Y after S75, I76V, A79P, V82A, E85K, S87R, A88P, I89M, L94Y, E96D, Y97G, D98Q, K99N, V100I, V101I, L102K, N104D, Y105I, E107N, V109I, G112E, R116S.

52. The designer BMP protein of embodiment 51, further comprising at least one mutation, the mutation not being within a Type I, Type IIA, or Type IIB binding domain of the designer BMP protein.

53. The designer BMP protein of embodiment 51, comprising the amino acid sequence of SEQ ID NO: 13.

54. The designer BMP protein of embodiment 51, having a binding profile which differs from a binding profile of a corresponding wild-type BMP.

55. The designer BMP protein of embodiment 54, wherein the binding profile of the designer BMP protein includes at least one of the following: binding to the ALK2 receptor with a $K_D$ not greater than about 2 nM; binding to the ALK3 receptor with a $K_D$ not greater than about 2 nM; binding to the ALK6 receptor with a $K_D$ not greater than about 1 nM; binding to the ActRIIA receptor with a $K_D$ not greater than about 2 nM; binding to the ActRIIB receptor with a $K_D$ not greater than about 0.5 nM; and binding to the BMPRIIA receptor with a $K_D$ not greater than about 3.5 nM.

56. A nucleic acid encoding the designer BMP protein of embodiment 51.

57. A method of producing a designer BMP protein comprising the steps of introducing an expression vector comprising the nucleic acid of embodiment 56 into a cell.

58. A method of treating a patient, comprising the step of contacting the patient with a designer BMP protein according to embodiment 51.

59. The method of embodiment 58, wherein treating a patient comprises treating a bone disease associated with bone loss, and wherein the step of contacting a patient with a designer BMP includes administering to the patient a dose of the designer BMP effective to treat the bone disease.

60. The method of embodiment 58, wherein treating a patient comprises treating fibrosis, and wherein the step of contacting a patient with a designer BMP includes administering to the patient a dose of the designer BMP effective to treat fibrosis.

61. A designer BMP protein comprising the following mutations relative to SEQ ID NO:2: V35I, P38R, Q41A, H46D, D48E, P50S, A54N, D55A, L57M, S59A, N70H, S71L, V72M, S74P, S75E, insertion of a Y after S75, I76V, A79P, V82A, E85K, S87R, A88P, I89M, L94Y, E96D, Y97G, D98Q, K99N, V100I, V101I, L102K, N104D, Y105I, E107N, V109I, G112E, R116S.

62. The designer BMP protein of embodiment 61, further comprising at least one mutation, the mutation not being within a Type I, Type IIA, or Type IIB binding domain of the designer BMP protein.

63. The designer BMP protein of embodiment 61, comprising the amino acid sequence of SEQ ID NO: 14.

64. The designer BMP protein of embodiment 61, having a binding profile which differs from a binding profile of a corresponding wild-type BMP.

65. The designer BMP protein of embodiment 64, wherein the binding profile of the designer BMP protein includes at least one of the following: binding to the ALK2 receptor with a $K_D$ not greater than about 2 nM; binding to the ALK3 receptor with a $K_D$ not greater than about 2 nM; binding to the ALK6 receptor with a $K_D$ not greater than about 1 nM; binding to the ActRIIA receptor with a $K_D$ not greater than about 2 nM; binding to the ActRIIB receptor with a $K_D$ not greater than about 0.5 nM; and binding to the BMPRIIA receptor with a $K_D$ not greater than about 3.5 nM.

66. A nucleic acid encoding the designer BMP protein of embodiment 61.

67. A method of producing a designer BMP protein comprising the steps of introducing an expression vector comprising the nucleic acid of embodiment 61 into a cell.

68. A method of treating a patient, comprising the step of contacting the patient with a designer BMP protein according to embodiment 61.

69. The method of embodiment 68, wherein treating a patient comprises treating a bone disease associated with bone loss, and wherein the step of contacting a patient with a designer BMP includes administering to the patient a dose of the designer BMP effective to treat the bone disease.

70. The method of embodiment 68, wherein treating a patient comprises treating fibrosis, and wherein the step of contacting a patient with a designer BMP includes administering to the patient a dose of the designer BMP effective to treat fibrosis.

71. A designer BMP protein comprising the following mutations relative to SEQ ID NO:2: V35I, P38R, Q41A, H46D, D48E, P50S, A54N, D55A, L57M, S59A, N70H, S71L, V72M, S74P, S75E, insertion of a Y after S75, I76V, A79P, V82A, E85K, S87R, A88P, I89M, L94Y, E96D, Y97G, D98Q, K99N, V100I, V101I, L102K, N104D, Y105I, E107N, V109I, G112E, R116S.

72. The designer BMP protein of embodiment 51, further comprising at least one mutation, the mutation not being within a Type I, Type IIA, or Type IIB binding domain of the designer BMP protein.

73. The designer BMP protein of embodiment 51, comprising the amino acid sequence of SEQ ID NO: 13.

74. The designer BMP protein of embodiment 51, having a binding profile which differs from a binding profile of a corresponding wild-type BMP.

75. The designer BMP protein of embodiment 54, wherein the binding profile of the designer BMP protein includes at least one of the following: binding to the ALK2 receptor with a $K_D$ not greater than about 2 nM; binding to the ALK3 receptor with a $K_D$ not greater than about 2 nM; binding to the ALK6 receptor with a $K_D$ not greater than about 1 nM; binding to the ActRIIA receptor with a $K_D$ not greater than about 2 nM; binding to the ActRIIB receptor with a $K_D$ not greater than about 0.5 nM; and binding to the BMPRIIA receptor with a $K_D$ not greater than about 3.5 nM.

76. A nucleic acid encoding the designer BMP protein of embodiment 51.

77. A method of producing a designer BMP protein comprising the steps of introducing an expression vector comprising the nucleic acid of embodiment 56 into a cell.

78. A method of treating a patient, comprising the step of contacting the patient with a designer BMP protein according to embodiment 51.

79. The method of embodiment 58 treating a bone disease associated with bone loss, and wherein the step of contacting a patient with a designer BMP includes administering to the patient a dose of the designer BMP effective to treat the bone disease.

80. The method of embodiment 58, wherein treating a patient comprises treating fibrosis, and wherein the step of contacting a patient with a designer BMP includes administering to the patient a dose of the designer BMP effective to treat fibrosis.

81. A designer BMP protein comprising the following mutations relative to SEQ ID NO: 2: V35I, P38E, Q41A, H46E, D48E, P50A, A54N, D55S, H56Y, L57M, S59A, N70H, S71F, V72I, insertion of a P after N73, S74E, S75T, 176V, A79P, V82A, E85K, S87R, A88P, 189M, L94Y, E96D, Y97G, D98Q, K99N, V100I, V101I, L102K, N104D, Y105I, E107N, V109I, G112E, R116S.

82. The designer BMP protein of embodiment 81, further comprising at least one mutation, the mutation not being within a Type I, Type IIA, or Type IIB binding domain of the designer BMP protein.

83. The designer BMP protein of embodiment 81, comprising the amino acid sequence of SEQ ID NO: 15.

84. The designer BMP protein of embodiment 81, having a binding profile which differs from a binding profile of a corresponding wild-type BMP.

85. The designer BMP protein of embodiment 84, wherein the binding profile of the designer BMP protein includes at least one of the following: binding to the ALK2 receptor with a $K_D$ not greater than about 2 nM; binding to the ALK3 receptor with a $K_D$ not greater than about 2 nM; binding to the ALK6 receptor with a $K_D$ not greater than about 1 nM; binding to the ActRIIA receptor with a $K_D$ not greater than about 2 nM; binding to the ActRIIB receptor with a $K_D$ not greater than about 0.5 nM; and binding to the BMPRIIA receptor with a $K_D$ not greater than about 3.5 nM.

86. A nucleic acid encoding the designer BMP protein of embodiment 81.

87. A method of producing a designer BMP protein comprising the steps of introducing an expression vector comprising the nucleic acid of embodiment 86 into a cell.

A method of treating a patient, comprising the step of contacting the patient with a designer BMP protein.

89. The method of embodiment 88, wherein treating a patient comprises treating a bone disease associated with bone loss, and wherein the step of contacting a patient with a designer BMP includes administering to the patient a dose of the designer BMP effective to treat the bone disease.

90. The method of embodiment 88, wherein treating a patient comprises treating fibrosis, and wherein the step of contacting a patient with a designer BMP includes administering to the patient a dose of the designer BMP effective to treat fibrosis.

CONCLUSION

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A designer bone morphogenetic protein (BMP) comprising the amino acid sequence of SEQ ID NO: 8.

2. The designer BMP of claim 1, having a binding profile which differs from the binding profile of corresponding wild-type BMP2.

3. The designer BMP of claim 2, wherein the binding profile of the designer BMP includes at least one of the following: binding to the Activin receptor-Like Kinase 2 (ALK2) receptor with a $K_D$ not greater than about 2 nM; binding to the Activin receptor-Like Kinase 3 (ALK3) receptor with a $K_D$ not greater than about 2 nM; binding to the Activin receptor-Like Kinase 6 (ALK6) receptor with a $K_D$ not greater than about 1 nM; binding to the Activin type IIA Receptor (ActRIIA) with a $K_D$ not greater than about 2 nM; binding to the Activin type IIB Receptor (ActRIIB) with a $K_D$ not greater than about 0.5 nM; and binding to the Bone Morphogenetic Protein type IIA Receptor (BMPRIIA) with a $K_D$ not greater than about 3.5 nM.

4. A nucleic acid encoding the designer BMP of claim 1.

5. A method of producing a designer BMP comprising the step of introducing an expression vector comprising the nucleic acid of claim 4 into a cell.

6. A designer BMP comprising an amino acid sequence selected from the group consisting of SEQ ID NO: 8, SEQ ID NO: 9, SEQ ID NO: 10, SEQ ID NO: 11, SEQ ID NO: 12, SEQ ID NO: 13, SEQ ID NO:14 and SEQ ID NO: 15.

7. The designer BMP of claim 6, comprising the amino acid sequence of SEQ ID NO: 9.

8. The designer BMP of claim 6, wherein the binding profile of the designer BMP includes at least one of the following: binding to the Activin receptor-Like Kinase 2 (ALK2) receptor with a $K_D$ not greater than about 2 nM; binding to the Activin receptor-Like Kinase 3 (ALK3) receptor with a $K_D$ not greater than about 2 nM; binding to the Activin receptor-Like Kinase 6 (ALK6) receptor with a $K_D$ not greater than about 1 nM; binding to the Activin type IIA Receptor (ActRIIA) with a $K_D$ not greater than about 2 nM; binding to the Activin type IIB Receptor (ActRIIB) with a $K_D$ not greater than about 0.5 nM; and binding to the Bone Morphogenetic Protein type IIA Receptor (BMPRIIA) with a $K_D$ not greater than about 3.5 nM.

9. A nucleic acid encoding the designer BMP of claim 6.

10. A method of producing a designer BMP comprising the step of introducing an expression vector comprising the nucleic acid of claim 9 into a cell.

* * * * *

SEQUENCE LISTING

<160> NUMBER OF SEQ ID NOS: 15

<210> SEQ ID NO 1
<211> LENGTH: 114
<212> TYPE: PRT
<213> ORGANISM: Homo sapiens

<400> SEQUENCE: 1

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg

<210> SEQ ID NO 2
<211> LENGTH: 116
<212> TYPE: PRT
<213> ORGANISM: Homo sapiens

<400> SEQUENCE: 2

Ser Pro Lys His His Ser Gln Arg Ala Arg Lys Lys Asn Lys Asn Cys
1               5                   10                  15

Arg Arg His Ser Leu Tyr Val Asp Phe Ser Asp Val Gly Trp Asn Asp
            20                  25                  30

Trp Ile Val Ala Pro Pro Gly Tyr Gln Ala Phe Tyr Cys His Gly Asp
        35                  40                  45

Cys Pro Phe Pro Leu Ala Asp His Leu Asn Ser Thr Asn His Ala Ile
    50                  55                  60

Val Gln Thr Leu Val Asn Ser Val Asn Ser Ser Ile Pro Lys Ala Cys
65                  70                  75                  80

Cys Val Pro Thr Glu Leu Ser Ala Ile Ser Met Leu Tyr Leu Asp Glu
                85                  90                  95

Tyr Asp Lys Val Val Leu Lys Asn Tyr Gln Glu Met Val Val Glu Gly
            100                 105                 110

Cys Gly Cys Arg
            115

<210> SEQ ID NO 3
<211> LENGTH: 138
<212> TYPE: PRT
<213> ORGANISM: Homo sapiens

<400> SEQUENCE: 3

Ala Ala Asn Lys Arg Lys Asn Gln Asn Arg Asn Lys Ser Ser Ser His
1               5                   10                  15

Gln Asp Ser Ser Arg Met Ser Ser Val Gly Asp Tyr Asn Thr Ser Glu
            20                  25                  30

-continued

```
Gln Lys Gln Ala Cys Lys Lys His Glu Leu Tyr Val Ser Phe Arg Asp
         35                  40                  45

Leu Gly Trp Gln Asp Trp Ile Ile Ala Pro Glu Gly Tyr Ala Ala Phe
 50                  55                  60

Tyr Cys Asp Gly Glu Cys Ser Phe Pro Leu Asn Ala His Met Asn Ala
 65                  70                  75                  80

Thr Asn His Ala Ile Val Gln Thr Leu Val His Leu Met Phe Pro Asp
                 85                  90                  95

His Val Pro Lys Pro Cys Cys Ala Pro Thr Lys Leu Asn Ala Ile Ser
            100                 105                 110

Val Leu Tyr Phe Asp Asp Ser Ser Asn Val Ile Leu Lys Lys Tyr Arg
        115                 120                 125

Asn Met Val Val Arg Ser Cys Gly Cys His
130                 135

<210> SEQ ID NO 4
<211> LENGTH: 139
<212> TYPE: PRT
<213> ORGANISM: Homo sapiens

<400> SEQUENCE: 4

Ser Ala Ser Ser Arg Arg Gln Gln Ser Arg Asn Arg Ser Thr Gln
 1               5                  10                  15

Ser Gln Asp Val Ala Arg Val Ser Ala Ser Asp Tyr Asn Ser Ser
                 20                  25                  30

Glu Leu Lys Thr Ala Cys Arg Lys His Glu Leu Tyr Val Ser Phe Gln
         35                  40                  45

Asp Leu Gly Trp Gln Asp Trp Ile Ile Ala Pro Lys Gly Tyr Ala Ala
 50                  55                  60

Asn Tyr Cys Asp Gly Glu Cys Ser Phe Pro Leu Asn Ala His Met Asn
 65                  70                  75                  80

Ala Thr Asn His Ala Ile Val Gln Thr Leu Val His Leu Met Asn Pro
                 85                  90                  95

Glu Tyr Val Pro Lys Pro Cys Cys Ala Pro Thr Lys Leu Asn Ala Ile
            100                 105                 110

Ser Val Leu Tyr Phe Asp Asp Asn Ser Asn Val Ile Leu Lys Lys Tyr
        115                 120                 125

Arg Asn Met Val Val Arg Ala Cys Gly Cys His
130                 135

<210> SEQ ID NO 5
<211> LENGTH: 139
<212> TYPE: PRT
<213> ORGANISM: Homo sapiens

<400> SEQUENCE: 5

Ser Thr Gly Ser Lys Gln Arg Ser Gln Asn Arg Ser Lys Thr Pro Lys
 1               5                  10                  15

Asn Gln Glu Ala Leu Arg Met Ala Asn Val Ala Glu Asn Ser Ser Ser
                 20                  25                  30

Asp Gln Arg Gln Ala Cys Lys Lys His Glu Leu Tyr Val Ser Phe Arg
         35                  40                  45

Asp Leu Gly Trp Gln Asp Trp Ile Ile Ala Pro Glu Gly Tyr Ala Ala
 50                  55                  60

Tyr Tyr Cys Glu Gly Glu Cys Ala Phe Pro Leu Asn Ser Tyr Met Asn
 65                  70                  75                  80
```

```
Ala Thr Asn His Ala Ile Val Gln Thr Leu Val His Phe Ile Asn Pro
            85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Asn Val Ile Leu Lys Lys Tyr
            115                 120                 125

Arg Asn Met Val Val Arg Ala Cys Gly Cys His
            130                 135
```

```
<210> SEQ ID NO 6
<211> LENGTH: 139
<212> TYPE: PRT
<213> ORGANISM: Homo sapiens

<400> SEQUENCE: 6

Ala Val Arg Pro Leu Arg Arg Arg Gln Pro Lys Lys Ser Asn Glu Leu
1               5                   10                  15

Pro Gln Ala Asn Arg Leu Pro Gly Ile Phe Asp Asp Val His Gly Ser
            20                  25                  30

His Gly Arg Gln Val Cys Arg Arg His Glu Leu Tyr Val Ser Phe Gln
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ser Phe Pro Leu Asp Ser Cys Met Asn
65                  70                  75                  80

Ala Thr Asn His Ala Ile Leu Gln Ser Leu Val His Leu Met Met Pro
            85                  90                  95

Asp Ala Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
            115                 120                 125

Arg Asn Met Val Val Lys Ala Cys Gly Cys His
            130                 135
```

```
<210> SEQ ID NO 7
<211> LENGTH: 110
<212> TYPE: PRT
<213> ORGANISM: Homo sapiens

<400> SEQUENCE: 7

Ser Ala Gly Ala Gly Ser His Cys Gln Lys Thr Ser Leu Arg Val Asn
1               5                   10                  15

Phe Glu Asp Ile Gly Trp Asp Ser Trp Ile Ile Ala Pro Lys Glu Tyr
            20                  25                  30

Glu Ala Tyr Glu Cys Lys Gly Gly Cys Phe Phe Pro Leu Ala Asp Asp
            35                  40                  45

Val Thr Pro Thr Lys His Ala Ile Val Gln Thr Leu Val His Leu Lys
    50                  55                  60

Phe Pro Thr Lys Val Gly Lys Ala Cys Cys Val Pro Thr Lys Leu Ser
65                  70                  75                  80

Pro Ile Ser Val Leu Tyr Lys Asp Asp Met Gly Val Pro Thr Leu Lys
            85                  90                  95

Tyr His Tyr Glu Gly Met Ser Val Ala Glu Cys Gly Cys Arg
            100                 105                 110
```

```
<210> SEQ ID NO 8
<211> LENGTH: 115
```

-continued

```
<212> TYPE: PRT
<213> ORGANISM: Artificial Sequence
<220> FEATURE:
<223> OTHER INFORMATION: Synthetic polypeptide

<400> SEQUENCE: 8

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Glu Gly Tyr Ala Ala Phe Tyr Cys Glu Gly Glu Cys Ala
        35                  40                  45

Phe Pro Leu Asn Ser Tyr Met Asn Ala Thr Asn His Ala Ile Val Gln
    50                  55                  60

Thr Leu Val His Phe Ile Asn Pro Glu Thr Val Pro Lys Pro Cys Cys
65                  70                  75                  80

Ala Pro Thr Glu Leu Asn Ala Ile Ser Val Leu Tyr Phe Asp Asp Ser
                85                  90                  95

Ser Asn Val Ile Leu Lys Asn Tyr Gln Asp Met Val Val Glu Gly Cys
            100                 105                 110

Gly Cys Arg
        115

<210> SEQ ID NO 9
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 9

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Glu Gly Tyr Ala Ala Phe Tyr Cys Glu Gly Glu Cys Ala
        35                  40                  45

Phe Pro Leu Asn Ser Tyr Met Asn Ala Thr Asn His Ala Ile Val Gln
    50                  55                  60

Thr Leu Val His Phe Ile Asn Pro Glu Thr Val Pro Lys Pro Cys Cys
65                  70                  75                  80

Ala Pro Thr Lys Leu Arg Pro Met Ser Met Leu Tyr Tyr Asp Asp Gly
                85                  90                  95

Gln Asn Ile Ile Lys Lys Asp Ile Gln Asn Met Ile Val Glu Glu Cys
            100                 105                 110

Gly Cys Ser
        115

<210> SEQ ID NO 10
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 10

Ser Pro Lys His His Ser Gln Arg Ala Arg Lys Lys Asn Lys Asn Cys
1               5                   10                  15

Arg Arg His Ser Leu Tyr Val Asp Phe Ser Asp Val Gly Trp Asn Asp
```

```
                        20                  25                  30

Trp Ile Ile Ala Pro Lys Gly Tyr Ala Ala Phe Tyr Cys Asp Gly Glu
             35                  40                  45

Cys Ser Phe Pro Leu Asn Ala His Met Asn Ala Thr Asn His Ala Ile
 50                  55                  60

Val Gln Thr Leu Val His Leu Met Asn Pro Glu Tyr Val Pro Lys Pro
 65                  70                  75                  80

Cys Cys Ala Pro Thr Glu Leu Asn Ala Ile Ser Val Leu Tyr Phe Asp
                 85                  90                  95

Asp Asn Ser Asn Val Ile Leu Lys Asn Tyr Gln Glu Met Val Val Glu
                100                 105                 110

Gly Cys Gly Cys Arg
            115

<210> SEQ ID NO 11
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 11

Ser Pro Lys His His Ser Gln Arg Ala Arg Lys Lys Asn Lys Asn Cys
 1               5                  10                  15

Arg Arg His Ser Leu Tyr Val Asp Phe Ser Asp Val Gly Trp Asn Asp
                 20                  25                  30

Trp Ile Ile Ala Pro Lys Gly Tyr Ala Ala Phe Tyr Cys Asp Gly Glu
             35                  40                  45

Cys Ser Phe Pro Leu Asn Ala His Met Asn Ala Thr Asn His Ala Ile
 50                  55                  60

Val Gln Thr Leu Val His Leu Met Asn Pro Glu Tyr Val Pro Lys Pro
 65                  70                  75                  80

Cys Cys Ala Pro Thr Lys Leu Arg Pro Met Ser Met Leu Tyr Tyr Asp
                 85                  90                  95

Asp Gly Gln Asn Ile Ile Lys Lys Asp Ile Gln Asn Met Ile Val Glu
                100                 105                 110

Glu Cys Gly Cys Ser
            115

<210> SEQ ID NO 12
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 12

Ser Pro Lys His His Ser Gln Arg Ala Arg Lys Lys Asn Lys Asn Cys
 1               5                  10                  15

Arg Arg His Ser Leu Tyr Val Asp Phe Ser Asp Val Gly Trp Asn Asp
                 20                  25                  30

Trp Ile Ile Ala Pro Arg Gly Tyr Ala Ala Phe Tyr Cys Asp Gly Glu
             35                  40                  45

Cys Ser Phe Pro Leu Asn Ala His Met Asn Ala Thr Asn His Ala Ile
 50                  55                  60

Val Gln Thr Leu Val His Leu Met Asn Pro Glu Tyr Val Pro Lys Pro
 65                  70                  75                  80
```

```
Cys Cys Ala Pro Thr Glu Leu Asn Ala Ile Ser Val Leu Tyr Phe Asp
                85                  90                  95

Asp Asn Ser Asn Val Ile Leu Lys Asn Tyr Gln Glu Met Val Val Glu
            100                 105                 110

Gly Cys Gly Cys Arg
        115

<210> SEQ ID NO 13
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 13

Ser Pro Lys His His Ser Gln Arg Ala Arg Lys Lys Asn Lys Asn Cys
1               5                   10                  15

Arg Arg His Ser Leu Tyr Val Asp Phe Ser Asp Val Gly Trp Asn Asp
            20                  25                  30

Trp Ile Ile Ala Pro Arg Gly Tyr Ala Ala Phe Tyr Cys Asp Gly Glu
            35                  40                  45

Cys Ser Phe Pro Leu Asn Ala His Met Asn Ala Thr Asn His Ala Ile
        50                  55                  60

Val Gln Thr Leu Val His Leu Met Asn Pro Glu Tyr Val Pro Lys Pro
65                  70                  75                  80

Cys Cys Ala Pro Thr Lys Leu Arg Pro Met Ser Met Leu Tyr Tyr Asp
                85                  90                  95

Asp Gly Gln Asn Ile Ile Lys Lys Asp Ile Gln Asn Met Ile Val Glu
            100                 105                 110

Glu Cys Gly Cys Ser
        115

<210> SEQ ID NO 14
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 14

Ser Pro Lys His His Ser Gln Arg Ala Arg Lys Lys Asn Lys Asn Cys
1               5                   10                  15

Arg Arg His Ser Leu Tyr Val Asp Phe Ser Asp Val Gly Trp Asn Asp
            20                  25                  30

Trp Ile Ile Ala Pro Glu Gly Tyr Ala Ala Phe Tyr Cys Glu Gly Glu
            35                  40                  45

Cys Ala Phe Pro Leu Asn Ser Tyr Met Asn Ala Thr Asn His Ala Ile
        50                  55                  60

Val Gln Thr Leu Val His Phe Ile Asn Pro Glu Thr Val Pro Lys Pro
65                  70                  75                  80

Cys Cys Ala Pro Thr Glu Leu Asn Ala Ile Ser Val Leu Tyr Phe Asp
                85                  90                  95

Asp Ser Ser Asn Val Ile Leu Lys Asn Tyr Gln Glu Met Val Val Glu
            100                 105                 110

Gly Cys Gly Cys Arg
        115

<210> SEQ ID NO 15
```

```
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 15

Ser Pro Lys His His Ser Gln Arg Ala Arg Lys Lys Asn Lys Asn Cys
1               5                   10                  15

Arg Arg His Ser Leu Tyr Val Asp Phe Ser Asp Val Gly Trp Asn Asp
                20                  25                  30

Trp Ile Ile Ala Pro Glu Gly Tyr Ala Ala Phe Tyr Cys Glu Gly Glu
            35                  40                  45

Cys Ala Phe Pro Leu Asn Ser Tyr Met Asn Ala Thr Asn His Ala Ile
    50                  55                  60

Val Gln Thr Leu Val His Phe Ile Asn Pro Glu Thr Val Pro Lys Pro
65                  70                  75                  80

Cys Cys Ala Pro Thr Lys Leu Arg Pro Met Ser Met Leu Tyr Tyr Asp
                85                  90                  95

Asp Gly Gln Asn Ile Ile Lys Lys Asp Ile Gln Asn Met Ile Val Glu
                100                 105                 110

Glu Cys Gly Cys Ser
            115
```